US012673009B2

(12) United States Patent
Sharpe et al.

(10) Patent No.: US 12,673,009 B2
(45) Date of Patent: Jul. 7, 2026

(54) DENTAL MATERIAL

(71) Applicants: King's College London, London (GB); Friedrich-Schiller-Universität Jena, Jena (DE)

(72) Inventors: Paul Thomas Sharpe, London (GB); Eileen Deirdre Gentleman, London (GB); Delia Silke Brauer, Jena (DE)

(73) Assignees: King's College London, London (GB); Friedrich-Schiller-Universität Jena, Jena (DE)

( * ) Notice: Subject to any disclaimer, the term of this patent is extended or adjusted under 35 U.S.C. 154(b) by 691 days.

(21) Appl. No.: 18/011,791

(22) PCT Filed: Jul. 2, 2021

(86) PCT No.: PCT/EP2021/068406
§ 371 (c)(1),
(2) Date: Dec. 20, 2022

(87) PCT Pub. No.: WO2022/003186
PCT Pub. Date: Jan. 6, 2022

(65) Prior Publication Data
US 2023/0310279 A1    Oct. 5, 2023

(30) Foreign Application Priority Data
Jul. 3, 2020    (GB) ...................................... 2010237

(51) Int. Cl.
*A61K 6/77*        (2020.01)
(52) U.S. Cl.
CPC .................................... *A61K 6/77* (2020.01)

(58) Field of Classification Search
CPC ...................................................... A61K 6/77
See application file for complete search history.

(56) References Cited

U.S. PATENT DOCUMENTS

| | | |
|---|---|---|
| 5,074,916 A | 12/1991 | Hench et al. |
| 5,769,638 A | 6/1998 | Torabinejad et al. |
| 5,891,233 A * | 4/1999 | Salonen ................... A61K 6/54 |
| | | 106/35 |
| 2003/0113686 A1 | 6/2003 | Jia et al. |
| 2003/0124483 A1 | 7/2003 | Jia et al. |
| 2004/0079258 A1 | 4/2004 | Hoeschleler et al. |
| 2004/0110864 A1 | 6/2004 | Hecht et al. |

(Continued)

FOREIGN PATENT DOCUMENTS

| | | |
|---|---|---|
| EP | 0279624 A2 | 8/1988 |
| WO | WO 2002/049581 A1 | 6/2002 |

(Continued)

OTHER PUBLICATIONS

Khorami, Mina et al., "In vitro bioactivity and biocompatibility of lithium substituted 45S5 bioglass" Materials Science and Engineering, 2011, pp. 1584-1592, vol. 31.

(Continued)

*Primary Examiner* — Michael F Pepitone
(74) *Attorney, Agent, or Firm* — KNOBBE, MARTENS, OLSON & BEAR, LLP

(57) ABSTRACT

A dental filling material or precursor thereof for use in therapy, which material comprises lithium and is capable of releasing lithium under physiological conditions.

19 Claims, 10 Drawing Sheets
Specification includes a Sequence Listing.

(56) References Cited

U.S. PATENT DOCUMENTS

| | | |
|---|---|---|
| 2004/0202985 A1 | 10/2004 | Karmaker et al. |
| 2005/0066854 A1 | 3/2005 | Jia et al. |
| 2005/0069836 A1 | 3/2005 | Jia et al. |
| 2008/0020353 A1 | 1/2008 | Jia et al. |
| 2008/0299513 A1 | 12/2008 | Jia et al. |
| 2011/0129802 A1 | 6/2011 | Jia et al. |
| 2011/0182995 A1 | 7/2011 | Asgary |
| 2017/0342383 A1 | 11/2017 | Deng et al. |
| 2020/0046801 A1 | 2/2020 | Helms et al. |

FOREIGN PATENT DOCUMENTS

| | | |
|---|---|---|
| WO | WO 2002/092021 A1 | 11/2002 |
| WO | WO 2007/144662 A1 | 12/2007 |
| WO | WO 2011/161422 A1 | 12/2011 |

OTHER PUBLICATIONS

Miguez-Pacheco, V. et al., "Development and characterization of lithium-releasing silicate bioactive glasses and their scaffolds for bone repair" Journal of Non-Crystalline Solids, 2016, pp. 65-72, vol. 432.

Moghanian, Amirhossein et al., "Synthesis and in vitro studies of sol-gel derived lithium substituted 58S bioactive glass" Ceramics international, 2017, pp. 12835-12843, vol. 43.

Silva, Jeison Gabriel Da et al., "Optimisation of lithium-substituted bioactive glasses to tailor cell response for hard tissue repair" Journal of Materials Science, 2017, pp. 8832-8844, vol. 52.

Yli-Urpo, Helena et al., "Compressive strength and surface characterization of glass ionomer cements modified by particles of bioactive glass" Dental Materials, 2005, pp. 201-209, vol. 21.

International Search Report for PCT/EP2021/068406 dated Nov. 5, 2021.

3M-ESPE. "Ketac™ Cem" Glass Ionomer Luting Cement—Technical Product Profile (Undated) in 40 pages.

3M-ESPE. "Ketac™ Cem Radiopaque Permanent Glass Ionomer Luting Cement". Sep. 25, 2017; Safety Data Sheet in 18 pages.

Bauer et al., Lithium Augmentation Therapy in Refractory Depression—Update 2002. Euro Arch Psych Clin Neuro. Jun. 2003;253: 132-139.

Bauer et al., Implications of the Neuroprotective Effects of Lithium for the Treatment of Bipolar and Neurodegenerative Disorders. Pharmacopsychiatry. Dec. 2003;36(S 3): 250-254.

Brauer D.S., Bioactive Glasses—Structure and Properties. Angew Chem Int Ed. 2015;54: 4160-4181.

Brauer et al., Sodium-free Mixed Alkali Bioactive Glasses. BioMed Glasses Dec. 14, 2016;2(1): 99-110.

Brauer et al., Benefits and Drawbacks of Zinc in Glass Ionomer Bone Cements. BioMed Mater. Jun. 17, 2011;6(4): 7 pages.

Brückner et al., Controlling the Ion Release from Mixed Alkali Bioactive Glasses by Varying Modifier Ionic Radii and Molar Volume. J Mater Chem B. 2016;4(18): 3121-3134.

Chen et al., Implication of Serum Concentration Monitoring in Patients with Lithium Intoxication. Psych Clin Neurosci. Feb. 2004;58(1): 25-29.

Cipriani et al., Lithium in the Prevention of Suicide in Mood Disorders: Updated Systematic Review and Meta-Analysis. BMJ. Jun. 27, 2013;346.

Clément-Lacroix et al., Lrp5-independent Activation of Wnt Signaling by Lithium Chloride Increases Bone Formation and Bone Mass in Mice. PNAS. Nov. 29, 2005;102(48): 17406-17411.

Crisp et al., Reactions in Glass Ionomer Cements: II. An Infrared Spectroscopic Study. J Dental Res. Nov. 1974;53(6): 1414-1419.

Del Ser et al., Treatment of Alzheimer's Disease with the GSK-3 Inhibitor Tideglusib: A Pilot Study. J Alzh Dis. Jan. 1, 2013;33(1): 205-215.

Fuchs et al., Therapeutic Ion-releasing Bioactive Glass Ionomer Cements with Improved Mechanical Strength and Radiopacity. Front Mater. 2015;2:Art.63 in 11 pages.

Gershon et al., Current Therapeutic Profile of Lithium. Arch Gen Psych. Jan. 1, 1997;54(1): 16-20.

Goldberg et al., Dentin: Structure, Composition and Mineralization: The Role of Dentin ECM in Dentin Formation and Mineralization. Front Biosci. (Elite Ed). Apr. 26, 2011;3: 711-735.

Hadis et al., Interaction of Hydraulic Calcium Silicate and Glass Ionomer Cements with Dentine. Materialia. Mar. 1, 2020;9: 100515 in 12 pages.

Han et al., The Cementogenic Differentiation of Periodontal Ligament Cells via the Activation of Wnt/β-catenin Signaling Pathway by Li+ Ions Released from Bioactive Scaffolds. Biomaterials. Sep. 1, 2012;33(27): 6370-6379.

Hench et al., The Sol-Gel Process. Chem Rev. Jan. 1, 1990;90(1): 33-72.

Ishimoto et al., Topical Application of Lithium Chloride on the Pulp Induces Dentin Regeneration. PLoS One. Mar. 26, 2015;10(3): e0121938 in 12 pages.

Kabacs et al., Lithium in Drinking Water and Suicide Rates Across the East of England. Br J Psych. May 2011;198(5): 406-407.

Kaur et al., MTA versus Biodentine: Review of Literature with a Comparative Analysis. J Clin. Diagn. Res. Aug. 2017;11(8): ZG01-ZG05.

Keller et al., Tooth Engineering: Searching for Dental Mesenchymal Cells Sources. Front Physiol. Mar. 4, 2011;2: 7 in 10 pages.

Klein et al., A Molecular Mechanism for the Effect of Lithium on Development. PNAS U.S. Aug. 6, 1996;93(16): 8455-8459.

Lim et al., Wnt Signaling Regulates Pulp Volume and Dentin Thickness. J Bone Min Res. Apr. 2014;29(4): 892-901.

Meijer et al., Pharmacological Inhibitors of Glycogen Synthase Kinase 3. Trends Pharmacol Sci.Sep. 1, 2004;25(9): 471-480.

Neves et al., Regulation of Reactionary Dentine Formation. J Dent Res. Apr. 2018;97(4):416-422.

Neves et al., Promotion of Natural Tooth Repair by Small Molecule GSK3 Antagonists. Sci Rep. Jan. 9, 2017;7(1):39654 in 7 pages.

Resilon Research, LLC., "Resilon™" Obturation Material—The New Standard off Care? Product Information Sheet; (Undated) in 10 pages.

Schwendicke et al., Interventions for Treating Cavitated or Dentine Carious Lesions (Protocol). Cochrane Lib Datab Syst Rev., 2018; 6:CD013039 in 15 pages.

Severus et al., What is the Optimal Serum Lithium Level in the Long-term Treatment of Bipolar Disorder—A review? Bipolar Disorders Mar. 2008;10(2): 231-237.

Shan et al., Lithium Chloride Promotes the Odontoblast Differentiation of Hair Follicle Neural Crest Cells by Activating Wnt/β-catenin Signaling. Cell Biol Int'l. Jan. 2015;39(1): 35-43.

Sidhu et al., A Review of Glass-Ionomer Cements for Clinical Dentistry. Journal of functional biomaterials. Jun. 28, 2016;7(3):15 pages.

Smith D.C., Development of Glass-Ionomer Cement Systems. Biomat. Apr. 1, 1998;19(6): 467-478.

Tolosa et al., A Phase 2 Trial of the GSK-3 Inhibitor Tideglusib in Progressive Supranuclear Palsy. Movement Disorders. Apr. 2014;29(4): 470-478.

Volponi et al., Tooth Repair and Regeneration. Curr Oral Health Rep. 2018;5: 295-303.

Wasson et al., A Study of the Relationship Between Setting Chemistry and Properties of Modified Glass-Poly(alkenoate) Cements. Br Polymer J. 1990;23(1-2): 179-183.

Whyte et al., Wnt Signaling and Injury Repair. Cold Spring Harbor Persp Biol. Aug. 1, 2012;4(8): a008078.

Wilson et al., Dental Silicate Cements: IX. Decomposition of the Powder. J Dental Res. Jan. 1970;49(1): 7-13.

Wilson et al., The Glass-Ionomer Cement; A New Translucent Dental Filling Material. J Appl Chem Biotech. Nov. 1971;21(11): 313.

Zhang et al., A Comparison of Lithium-Substituted Phosphate and Borate Bioactive Glasses for Mineralised tissue Repair. Dent Mater. Jun. 1, 2019;35(6): 919-927.

* cited by examiner a)

b)

c)

- ● — GIC
- ■ — 10% Li0GIC
- ▲ — 10% LithGlassGIC
- ▼ — 15% LithGlassGIC
- ◆ — 20% LithGlassGIC
- ○ — 25% LithGlassGIC
- □ — 30% LithGlassGIC
- △ — 40% LithGlassGIC d)

e)

f)

- ● GIC
- ■ 10% Li0GIC
- ▲ 10% LithGlassGIC
- ▼ 15% LithGlassGIC
- ◆ 20% LithGlassGIC
- ○ 25% LithGlassGIC
- ▫ 30% LithGlassGIC
- △ 40% LithGlassGIC

FIG. 5 (continued)

SEQUENCE LISTING

```
<160> NUMBER OF SEQ ID NOS: 4

<210> SEQ ID NO 1
<211> LENGTH: 20
<212> TYPE: DNA
<213> ORGANISM: Mus musculus

<400> SEQUENCE: 1
ggctgtattc ccctccatcg                                      20

<210> SEQ ID NO 2
<211> LENGTH: 22
<212> TYPE: DNA
<213> ORGANISM: Mus musculus

<400> SEQUENCE: 2
ccagttggta acaatgccat gt                                    22

<210> SEQ ID NO 3
<211> LENGTH: 21
<212> TYPE: DNA
<213> ORGANISM: Mus musculus

<400> SEQUENCE: 3
tgactctcct tccagatccc a                                     21

<210> SEQ ID NO 4
<211> LENGTH: 19
<212> TYPE: DNA
<213> ORGANISM: Mus musculus
```

-continued

<400> SEQUENCE: 4
tgcccacact aggctgaca                                                                    19

DENTAL MATERIAL

CROSS REFERENCE TO RELATED APPLICATIONS

This application is a U.S. National Phase Application of PCT International Application Number PCT/EP2021/068406, filed on Jul. 2, 2021, designating the United States of America and published in the English language, which is an International Application of and claims the benefit of priority to United Kingdom Patent Application No. 2010237.2, filed on Jul. 3, 2020. The disclosures of the above-referenced applications are hereby expressly incorporated by reference in their entireties.

REFERENCE TO SEQUENCE LISTING

A Sequence Listing submitted as an ASCII text file via EFS-Web is hereby incorporated by reference in accordance with 37 U.S.C. § 1.52 (e). The name of the ASCII text file for the Sequence Listing is SeqList-GRVS001-001APC.txt, the date of creation of the ASCII text file is Dec. 19, 2022, and the size of the ASCII text file is 984 bytes.

TECHNICAL FIELD

This invention relates to dental filling materials or precursors thereof, in particular, though not exclusively, for use in therapy. Aspects of the invention also relate to kits for preparing a dental filling material.

BACKGROUND

The restoration of tooth mineral after tooth damage is central to clinical dental practice. Tooth mineral can become damaged following trauma or infection (caries). Depending on the extent of the damage, it may affect the various parts of a tooth, the principal components being the enamel (1), the dentine (2), the pulp (3) and the cementum (4), shown in FIG. 1. The damage can result in the inner parts of the tooth becoming exposed to the external environment and becoming infected.

If a tooth still has sound external structures, the approach to repairing dental damage commonly involves excising the affected parts of the tooth and replacing these excised portions by putting one or more filling materials into the resulting cavity. Generally, a dentist packs the filling material into the cavity and shapes it appropriately while the material is still malleable. The material is then cured or allowed to harden, resulting in a dental "filling".

When filling material is placed downward into the tooth from the upper or crown region of the tooth, it is typically referred to as an "orthograde" filling. When filling material is placed into the tooth from the root tip (usually accessed via incisions into the gum and jaw bone), it is referred to as an "retrograde" filling.

There is a variety of different dental filling materials for different types of tooth damage. Current approaches to restoration are dominated by materials aimed at producing a hard, easy-to-use, and long-lasting restoration.

Dental lesions can penetrate a tooth to different depths. Some dental lesions penetrate the enamel but not the dentine. In more significant dental lesions, as shown in FIG. 2, the lesion (5) penetrates the enamel and enters the dentine, but does not penetrate into the pulp. In deeper dental lesions, the lesion penetrates all the way through the enamel and the dentine and into the dental pulp.

The clinical repair of tooth damage which has penetrated through the enamel and into the dentine and/or the pulp usually involves the use of two different materials. The first material is applied to seal off or cap the exposed dentine and/or pulp and as a protective base/liner under dental filling materials. These capping materials are often referred to as pulp capping materials, which can be defined further as indirect pulp capping materials and direct pulp capping materials. Direct pulp capping materials are used in cases where pulp is exposed, and hence the pulp is capped directly. Indirect pulp capping materials are used in cases where the dentine is damaged but the pulp is not exposed, and hence the pulp is capped indirectly.

Materials which are commonly used as pulp capping materials, i.e. to seal off the exposed dentine and/or pulp from the external environment, include calcium hydroxide compositions such as Dycal (Dentsply, 623801) and inorganic hydraulic silicate cements such as mineral trioxide aggregate (MTA) or Biodentine®. In addition to these pulp capping materials, a dentist would fill the rest of the cavity with a hard long-lasting permanent filling material such as glass ionomer cements, resin composites or other permanent fillings.

Many filling materials are prepared by a dentist or dental surgeon in situ by combining a dental filling powder with a liquid to form a malleable cement. This malleable material can be placed in the tooth cavity and shaped as required, after which the material is allowed to set over time or cured, for example with the assistance of UV light, resulting in a hard filling.

Glass ionomer cements (GIC), which are based on an aluminosilicate glass reacting with a poly acid, were originally developed in the 1970s (Wilson and Kent, 1970, Wilson and Kent, 1971, Smith, 1998) because of the limitations of other restorative materials (Wilson and Kent, 1971, Crisp et al., 1974, Wasson and Nicholson, 1990, Brauer et al., 2011, Brauer, 2015, Fuchs et al., 2015). GIC have better aesthetics than amalgam, gold and porcelain and so are often used for luting, lining and restoration.

A need remains for ways to improve the treatment of dental damage, and especially for ways to improve the restoration of dentine following dental damage.

SUMMARY OF THE INVENTION

An aspect of the invention provides a dental filling material or precursor thereof for use in therapy, which material comprises lithium and is capable of releasing lithium under physiological conditions.

Another aspect of the invention provides a dental filling material or precursor thereof for use in therapy, wherein the material or precursor thereof comprises a bioactive glass comprising lithium.

A further aspect of the invention provides a dental filling material or precursor thereof for use in therapy, wherein the dental filling material comprises a dental cement comprising lithium.

Still another aspect of the invention provides a dental filling material or precursor thereof comprising a glass component, the glass component comprising a bioactive glass comprising lithium, wherein the bioactive glass is present in the glass component in an amount of at least 10 wt %.

Still a further aspect of the invention provides a method of repairing dentine or treating damage to dentine, which comprises administering to a patient in need thereof a dental filling material or precursor thereof in accordance with any aspect or embodiment of the invention.

Throughout the description and claims of this specification, the words "comprise" and "contain" and variations of the words, for example "comprising" and "comprises", mean "including but not limited to", and do not exclude other components, integers or steps. Moreover the singular encompasses the plural unless the context otherwise requires: in particular, where the indefinite article is used, the specification is to be understood as contemplating plurality as well as singularity, unless the context requires otherwise.

Preferred features of each aspect of the invention may be as described in connection with any of the other aspects. Within the scope of this application it is expressly intended that the various aspects, embodiments, examples and alternatives set out in the preceding paragraphs, in the claims and/or in the following description and drawings, and in particular the individual features thereof, may be taken independently or in any combination. That is, all embodiments and/or features of any embodiment can be combined in any way and/or combination, unless such features are incompatible.

BRIEF DESCRIPTION OF THE DRAWINGS

One or more embodiments of the invention will now be described, by way of example only, with reference to the accompanying drawings, in which.

(A-H) MicroCT images of upper first molars after 4 weeks of treatments with (A) glass ionomer cements (GIC) (n=6), (B) 10% Lith0GIC (n=6), (C) 10% LithGlassGIC (n=6), (D) 15% LithGlassGIC (n=6), (E) 20% LithGlassGIC (n=6), (F) 25% LithGlassGIC (n=6), (G) 30% LithGlassGIC (n=6), (H) 40% LithGlassGIC (n=6), white squares indicate the area of newly formed dentin under the drilling site.

(A'-H') histology of reactionary dentin formation after 4 weeks of treatments.

(A"-H") higher magnification of red squares in A'-H' images show tubular reactionary dentin under capping materials.

All teeth were drilled in CD1 wild-type mice. Images show sagittal sections of teeth and an asterisk indicates a drilling site. (P<0.0001).

(I) microCT analysis of newly formed dentin under capping materials.

(J) microCT linear measurement from the point where the dentin was drilled to the top of the middle pulp horn.

DETAILED DESCRIPTION

Aspects of the invention provide or utilise a dental filling material or precursor thereof.

Suitably, the dental filling material comprises lithium and is capable of releasing lithium under physiological conditions. Advantageously, the material may release a therapeutically effective amount of lithium under physiological conditions.

Preferably, the material may release a therapeutically effective amount of lithium under physiological conditions in less than 24 hours, more preferably in less than 1 hour.

In an embodiment of the invention, the dental filling material or precursor thereof is for use in dental therapy.

Preferably, the dental filling material or precursor thereof is for use in dentine repair, or for use in treating damage to dentine.

Figure 1:
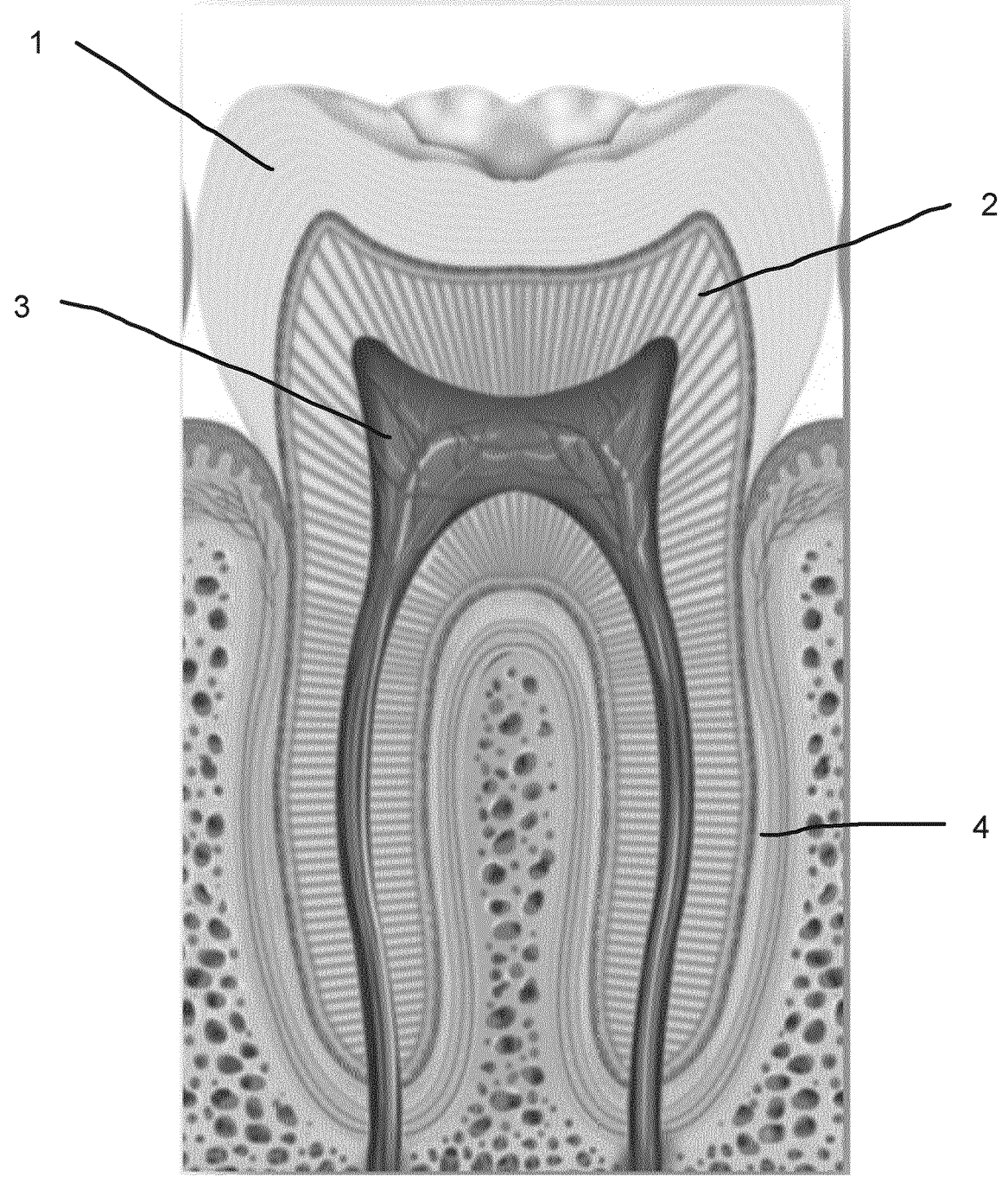
FIG. 1 shows a longitudinal section of a healthy tooth showing two roots.

Dentine is a vital tooth mineral. As indicated in FIG. 1, dentine (2) forms a thick layer of porous mineral beneath the enamel (1) that serves as a second barrier of defence against infectious agents threatening the inner soft pulp tissue (3). The dental pulp houses mesenchyme-derived specialised cells, the odontoblasts, that are responsible for dentine secretion throughout life. The odontoblasts are located in the pulp at the interface with the dentine.

In response to dentine and/or odontoblast damage, tertiary dentine forms in a natural reparative/regenerative process. In deep caries lesions that penetrate the pulp and destroy odontoblasts, resident pulp stem cells are activated and differentiate into odontoblast-like cells that produce "reparative dentine". In lesions that do not expose the pulp, signals from the damaged dentine stimulate odontoblast activity to produce "reactionary dentine" which forms on the pulpal aspect of the resident dentine (Goldberg et al., 2011, Vishwakarma et al., 2014, Neves and Sharpe, 2018).

The inventors have shown that it is possible to incorporate lithium in a dental filling material or precursor thereof, which lithium is released under physiological conditions, and can be delivered to the dental pulp.

It is known to be difficult to deliver medicaments (such as therapeutic agents) to the dental pulp if the pulp cavity has not been exposed. In the present invention, surprisingly, the lithium is not only released from the dental filling material, but the lithium ions are able to penetrate any remaining dentine and stimulate odontoblast activity to promote reactionary dentine formation.

As shown in the Examples, it has been found that lithium-releasing dental filling material can promote reactionary dentine formation in a mouse molar tooth damage model, resulting in restoration of the thickness of the dentine layer below the damage site.

In an embodiment, the dental filling material or precursor thereof is for use in treating a dental lesion wherein the pulp is not exposed. Preferably, the dental filling material or precursor thereof is for use in treating a dental lesion wherein dentine is exposed but the pulp is not exposed.

Figure 2:
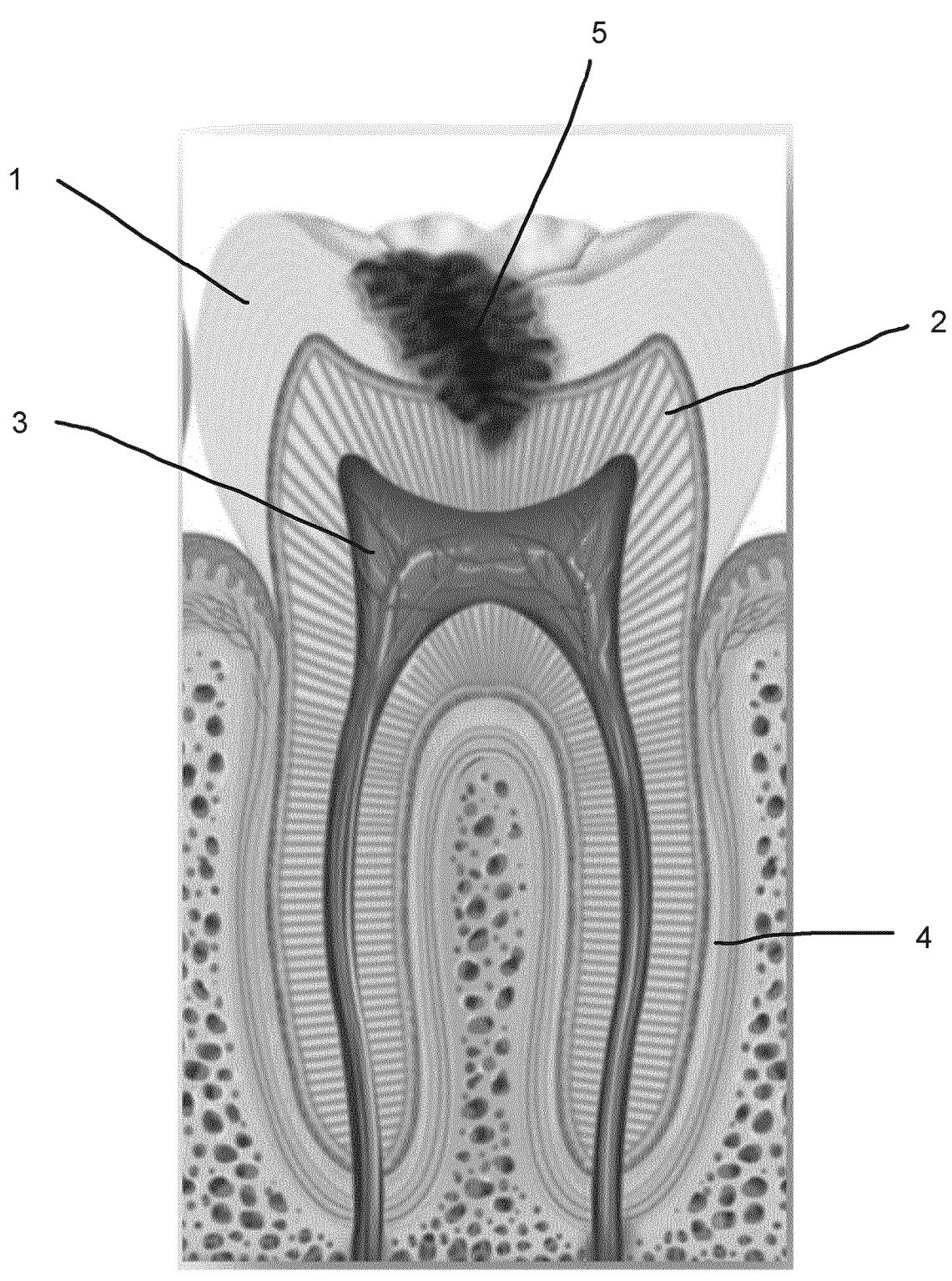
FIG. 2 shows a longitudinal section of a tooth where decay has penetrated through the enamel (1) and dentine (2) but has not reached the pulp (3).
Figure 3:
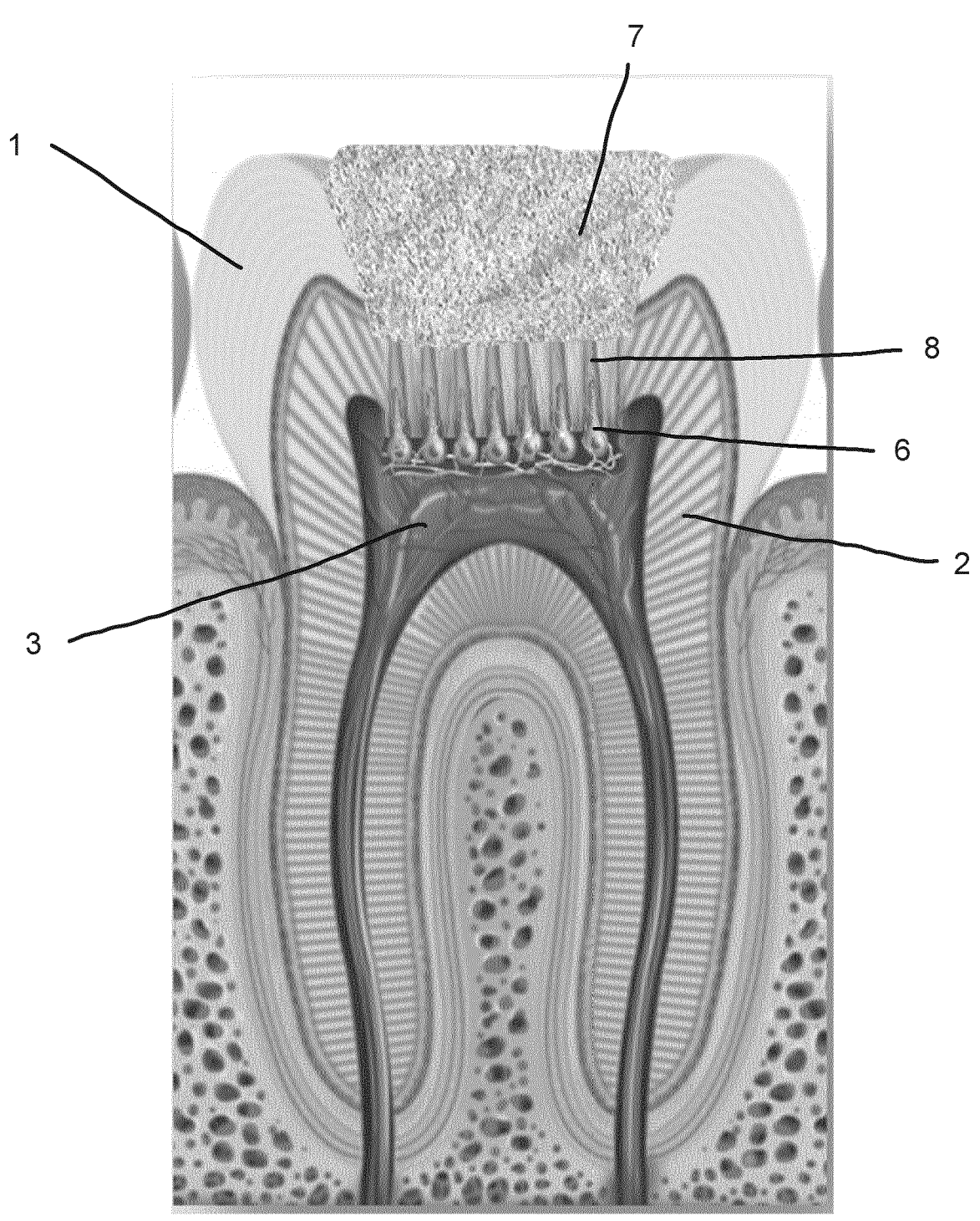
FIG. 3 shows a longitudinal section of a tooth where decay has been excised and the resulting cavity has been filled with dental filling material (7).

Such a dental lesions is shown in FIG. 2, where a lesion (5) can be seen to penetrate though the enamel (1) and into the dentine (2), but the pulp (3) is not exposed. This type of dental lesion, also referred to as shallow lesion, can be treated by first excising the affected parts of the tooth in the usual way, which creates a cavity. With reference to FIG. 3, the cavity which has been created by excising the affected parts of the tooth can then be filled with the dental filling material (7) in accordance with the present invention.

When there is still a layer of dentine (2) on the pulp (3), the original odontoblasts (6) may not be destroyed (odontoblasts not shown to scale in FIG. 3). Surprisingly, the lithium can not only be released from the dental filling material (7), but the lithium ions can penetrate the dentine (2) through the dentinal tubules (8) (not shown to scale in FIG. 3), and can stimulate the odontoblasts (6) to promote reactionary dentine formation.

Figure 4:
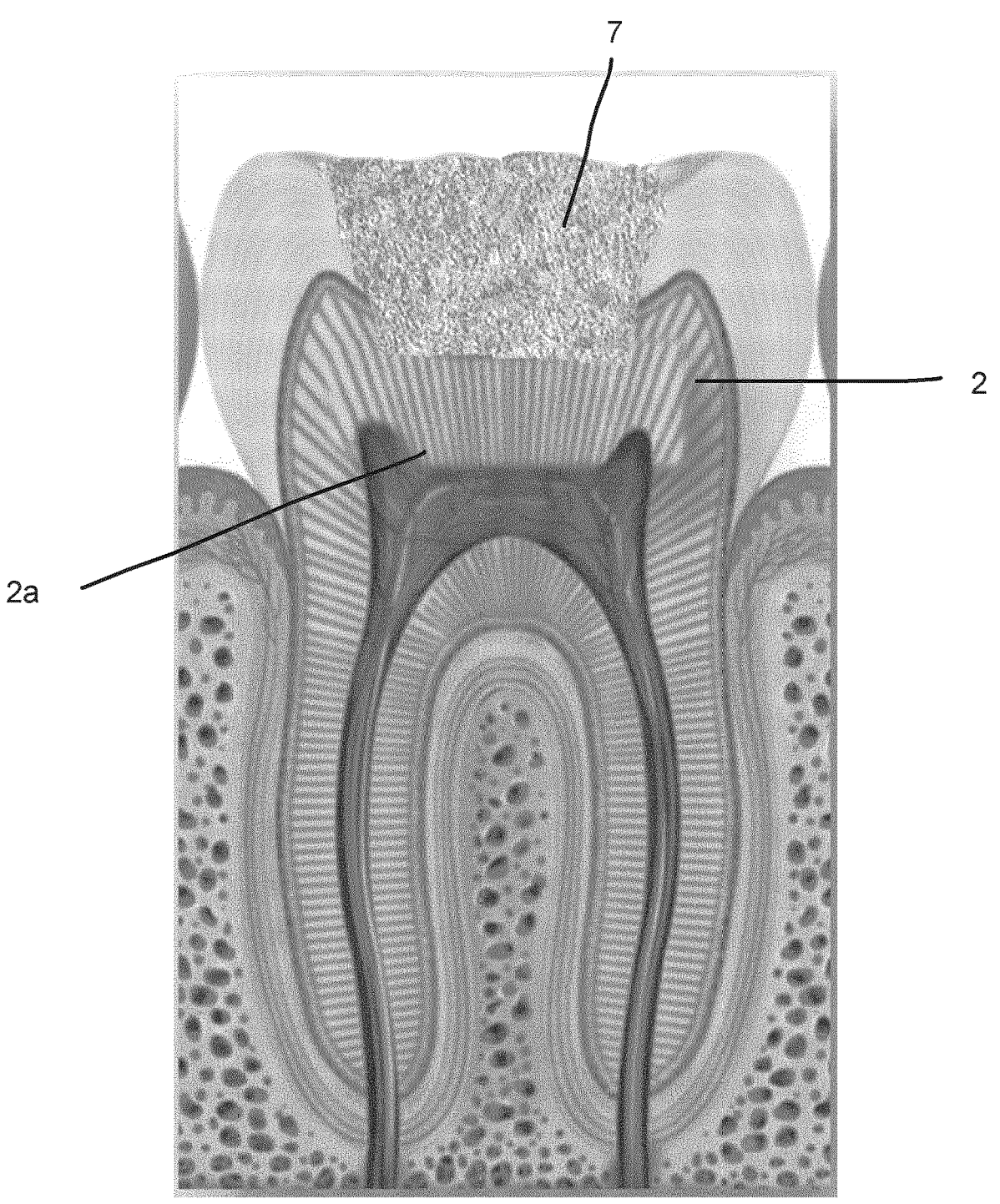
FIG. 4 shows a longitudinal section of a tooth where reactionary dentine has been formed and the thickness of the dentine layer has been restored.

As shown in FIG. 4, the lithium-releasing dental filling material (7) can promote the formation of reactionary dentine (2a) below the damage site, resulting in restoration of the thickness of the dentine layer.

In current dental therapy, damage to dentine is usually treated by applying two different dental filling materials, namely an indirect pulp capping material to seal off the exposed dentine from the external environment, and a permanent filling material to fill the rest of the tooth cavity.

The inventors have shown that it is possible to use a single dental filling material, which can be applied by a dentist or dental surgeon in a single sitting, which both stimulates dentine regeneration and provides a filling in the cavity at the same time, with good levels of hardness and durability. No separate cavity filling is therefore required: the damaged dentine is reinforced from the pulp side and the cavity filling is already in place.

In an embodiment, the dental filling material or precursor thereof comprises a bioactive glass comprising lithium.

Bioactive glasses have been used clinically in bone and dental restorations for more than 30 years, and have well-described surface reactive properties, which allow them to directly bond to biological tissues.

Bioactive glasses are a group of surface-reactive glass-ceramics designed to induce biological activity that results in the formation of a strong bond between the bioactive glass and living tissue such as bone. Generally, a biologically active or bioactive material is one which, when implanted into living tissue, induces formation of an interfacial bond between the material and the surrounding tissue. The bioactivity of silicate glasses was first observed in soda-calcia-phospho-silica glasses in 1969, resulting in the development of a bioactive glass comprising calcium salts, phosphorous, sodium salts and silicon. These glasses comprised $SiO_2$, CaO, $Na_2O$ and $P_2O_5$, and optionally $CaF_2$ and/or $B_2O_3$.

Bioactive glasses are for example described in WO 2007/144662 and WO 2011/161422.

A particular example of a bioactive glass, which is manufactured commercially as Bioglass® 45S5, is composed of 45 wt % $SiO_2$, 24.5 wt % CaO, 6.0 wt % $P_2O_5$ and 24.5 wt % $Na_2O$; corresponding to 46.1 mole % $SiO_2$, 26.9 mole % CaO, 2.6 mole % $P_2O_5$ and 24.4 mole % $Na_2O$.

In a preferred embodiment of the invention, the dental filling material or precursor thereof comprises a bioactive glass comprising lithium. In an embodiment, the dental filling material or precursor thereof comprises the bioactive glass in an amount of at least 0.1 wt %, at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, or at least 99 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

The dental filling material or precursor thereof may comprise a glass component. The bioactive glass comprising lithium may form all or part of said glass component.

The dental filling material may suitably comprise other components in addition to the glass component.

The precursor of the dental filling material may comprise other components in addition to the glass component, or may consist of the glass component.

In an embodiment, the dental filling material or precursor thereof comprises a glass component in an amount of at least 1 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, or at least 95 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

In an embodiment, the bioactive glass comprising lithium forms at least part of the glass component of the dental filling material or precursor thereof. The glass component, or indeed the dental filling material or precursor as a whole, may, for example, comprise the bioactive glass in an amount of at least 0.1 wt %, at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, or at least 99 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

In some embodiments, it is preferred to use a high concentration of the bioactive glass comprising lithium. Suitably, the bioactive glass may be present in the glass component, or indeed in the dental filling material or precursor as a whole, in an amount of at least 10 wt %. For example, the glass component, or the dental filling material or precursor as a whole, may comprise the bioactive glass in an amount of at least 10 wt %, at least 11 wt %, at least 12 wt %, at least 13 wt %, at least 14 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, or at least 99 wt %. Additionally or alternatively the glass component, or the dental filling material or precursor as a whole, may comprise the bioactive glass in an amount up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, or up to 15 wt %.

In addition to the bioactive glass comprising lithium, the glass component may further comprise other types of glass. Such types of glass are well-known for dental applications, such as for example the glasses described in Sidhu, S. K. et al., J. Funct. Biomater. 2016, 7, 16; doi:10.3390/jfb7030016.

In another embodiment, the bioactive glass comprising lithium is the only glass in the dental filling material or precursor thereof. The glass component of the dental filling material or precursor thereof may consist of the bioactive glass comprising lithium.

Additionally or alternatively the glass component may be the sole glass component of the dental filling material or precursor thereof.

In a preferred embodiment of the invention, the bioactive glass comprises a source of lithium. This source of lithium can for example include, but is not limited to, lithium oxide ($Li_2O$) or lithium carbonate ($Li_2CO_3$). The incorporation of $Li_2O$ or $Li_2CO_3$ in the bioactive glass allows lithium to be released from the bioactive glass under physiological conditions. In a preferred embodiment, the bioactive glass comprises $Li_2O$.

In a preferred embodiment, the bioactive glass comprises a source of lithium at a molar percentage of at least 0.01%, at least 0.1%, at least 1%, at least 2%, at least 3%, at least 4%, at least 5%, at least 10%, at least 15%, or at least 20%; and/or up to 60%, up to 55%, up to 50%, up to 45%, up to 40%, up to 45%, up to 30%, or up to 25%; for example at a molar percentage of from 5% to 30%. Preferably, the source of lithium is $Li_2O$ or $Li_2CO_3$, more preferably $Li_2O$.

The inventors have found that it is possible to replace some or all of the $Na_2O$ in known commercial bioactive glasses, such as for example Bioglass® 45S5, with $Li_2O$. Preliminary work and limited in vitro testing was reported in da Silva et al., 2017, Journal of materials science, 52, 8832-8844.

In a preferred embodiment, the combined molar percentage of the $Li_2O$ and any $Na_2O$ in the bioactive glass is at least 0.1%, at least 1%, at least 2%, at least 3%, at least 4%, at least 5%, at least 10%, at least 15%, or at least 20%; and/or up to 50%, up to 40%, up to 30%, or up to 25%.

The molar ratio of $Li_2O$ to $Na_2O$ in the bioactive glass can range from 0.1:99.9 to 100:0. Preferably, the molar ratio of $Li_2O$ to $Na_2O$ in the bioactive glass may be at least 0.1: 99.999, at least 1:99, at least 5:95, at least 25:75, at least 50:50, or at least 75:25.

The bioactive glass may additionally comprise silicon dioxide ($SiO_2$). Preferably, the bioactive glass comprises $SiO_2$ at a molar percentage of from 10%, from 15%, from 20%, from 25%, from 30%, from 35%, from 40%, from 45% or from 50%; and or up to 90%, up to 80%, up to 70%, up to 60%, or up to 50%.

The bioactive glass may also comprise one or more additional components. The additional components may comprise one or more of calcium, phosphate, magnesium, zinc, boron or fluorine and an alkali metal such as sodium and potassium. These components may, for example, be provided as compounds including but not limited to sodium oxide ($Na_2O$), sodium carbonate ($Na_2CO_3$), sodium nitrate ($NaNO_3$), sodium sulphate ($Na_2SO_4$), sodium silicates, potassium oxide ($K_2O$), potassium carbonate ($K_2CO_3$), potassium nitrate ($KNO_3$), potassium sulphate ($K_2SO_4$), potassium silicates, calcium oxide (CaO), calcium carbonate ($CaCO_3$), calcium nitrate ($Ca(NO_3)_2$), calcium sulphate ($CaSO_4$), calcium silicates, magnesium oxide (MgO), magnesium carbonate ($MgCO_3$), magnesium nitrate ($Mg(NO_3)_2$), magnesium sulphate ($MgSO_4$), magnesium silicates, zinc oxide (ZnO), zinc carbonate ($ZnCO_3$), zinc nitrate ($Zn(NO_3)_2$), zinc sulphate ($ZnSO_4$), and zinc silicates and any such compounds, including acetates of sodium, potassium, calcium, magnesium or zinc, that decompose to form an oxide.

The bioactive glass may comprise a source of sodium ions at a molar percentage of from 0 to 30%, from 0 to 25%, from 0 to 20%, from 3 to 25%, from 5 to 25%, from 0 to 15% or from 0 to 10%. Preferably the source of sodium ions is sodium oxide ($Na_2O$).

The bioactive glass may comprise a source of potassium ions at a molar percentage of from 0 to 30%, from 0 to 25%, from 0 to 20%, from 3 to 25%, from 5 to 25%, from 0 to 15% or from 0 to 10%. Preferably the source of potassium ions is potassium oxide ($K_2O$).

In an embodiment, the bioactive glass is free from sodium and/or potassium.

The bioactive glass preferably comprises a source of calcium including but not limited to calcium oxide (CaO), calcium carbonate ($CaCO_3$), calcium nitrate ($Ca(NO_3)_2$), calcium sulphate ($CaSO_4$), calcium silicates or a source of calcium oxide. Preferably the source of calcium is CaO. For the purposes of this invention, a source of calcium oxide includes any compound that decomposes to form calcium oxide.

The molar percentage of calcium may be from 0% to 50%, from 0% to 40%, from 0 to 30%, from 5 to 30%, from 10 to 30%, or from 20 to 30%. Preferably, the bioactive glass comprises CaO at a molar percentage of from 0% to 50%, from 0% to 40%, from 0 to 30%, from 5 to 30%, from 10 to 30%, or from 20 to 30%.

The bioactive glass of the present invention may comprise $P_2O_5$. Preferably, the bioactive glass comprises $P_2O_5$ at a molar percentage of from is 0% to 15%, from 0% to 10%, from 0 to 5%, or from 1 to 5%.

The bioactive glass may additionally comprise a source of magnesium such as for example magnesium oxide (MgO), magnesium carbonate ($MgCO_3$), magnesium nitrate ($Mg(NO_3)_2$), magnesium sulphate ($MgSO_4$), magnesium silicates and any such compounds that decompose to form magnesium oxide; a source of zinc, including but not limited to zinc oxide (ZnO), zinc carbonate ($ZnCO_3$), zinc nitrate ($Zn(NO_3)_2$), zinc sulphate ($ZnSO_4$), and zinc silicates and any such compounds that decompose to form zinc oxide; boron, for example as $B_2O_3$; fluorine, for example in the form of one or more of calcium fluoride ($CaF_2$), strontium fluoride ($SrF_2$), magnesium fluoride ($MgF_2$), sodium fluoride (NaF) or potassium fluoride (KF); and/or silver, for example in the form of silver oxide.

The bioactive glass may be provided as, for example, a melt-derived bioactive glass or a sol-gel derived bioactive glass and can be prepared using known melt quench or sol gel techniques. The melt-derived or sol-gel derived bioactive glass can further be sintered using known technology.

In an embodiment, the bioactive glass may be a melt-derived bioactive glass. Melt-derived bioactive glasses can be prepared by mixing and blending grains of the appropriate carbonates or oxides, melting and homogenising the mixture at temperatures of approximately 1250° C. to 1500° C. The mixture is then cooled, preferably by pouring the molten mixture into a suitable liquid such as deionised water, to produce a glass frit.

In an embodiment, the bioactive glass may be a sol-gel derived bioactive glass. The production of ceramic and glass materials by the sol-gel process has been known for many years and is described in for example U.S. Pat. No. 5,074,916 and Hench & West, The Sol-Gel Process, 90 Chem. Rev. 33 (1990). The sol-gel process essentially involves mixing of the glass precursors (metal alkoxides in solution) into a sol (a dispersion of colloidal particles in a liquid), followed by hydrolysis, gelation and firing at a temperature of approximately 200-900° C. The mixture is cast in a mould prior to gelation of the mixture, in which the colloidal sol particles link together to form a rigid and porous three-dimensional network which can be aged, dried, chemically stabilised and/or densified to produce structures with ranges of physical properties. All of these steps can be carried out at relatively low temperatures as compared with melt derived processes, typically 600-800° C.

Preferably, the bioactive glass may have a particle diameter suitable for use in dental applications. The bioactive glass can, for example, be in the form of glass particles with a maximum particle diameter below 1 mm, below 900 μm, below 800 μm, below 700 μm, below 600 μm, below 500 μm, below 400 μm, below 300 μm, below 200 μm, below 100 μm, below 90 μm, below 80 μm, below 70 μm, below 60 μm, below 50 μm, below 40 μm, or below 38 μm. The maximum particle diameter can be determined by sieving the particles through an appropriately sized mesh.

The particle size and size distribution of the glass can be adjusted using conventional techniques, such as grinding, screening, sedimentation or other particle classification methods.

In an embodiment of the invention, the dental filling material comprises or consists of a dental cement comprising lithium.

Dental cements are widely used in dental therapy. Dental cements are commonly prepared by a dentist or dental surgeon in situ by mixing a dental cement powder (a precursor) with a liquid, in order to form a malleable cement. This malleable material can be placed in the tooth cavity and shaped as required, after which the material is allowed to set over time and/or cured, for example with the assistance of UV light, which results in a filling with good levels of hardness and durability.

Preferably, the dental cement or precursor thereof comprises a bioactive glass comprising lithium. More preferably, the bioactive glass in the dental cement is a bioactive glass comprising lithium as defined above.

In an embodiment, the dental cement comprising lithium is a glass ionomer cement comprising lithium.

Glass ionomer cements (GICs) are formed via an acid-base reaction between polymeric acids (such as e.g. poly (acrylic acid)) and powdered glasses of basic character.

As is well-known in the art, the three main ingredients of a glass ionomer cement are the polymeric (and usually water-soluble) acid, the basic glass, and water. Glasses used in ionomer cements are commonly aluminosilicate glasses, optionally with fluoride and phosphate additions. Existing commercial glasses for glass-ionomer cements also typically contain calcium and/or sodium compounds. Like most dental cements, glass ionomer cements are commonly prepared by a dentist or dental surgeon in situ by mixing a GIC powder (a precursor) with a liquid, in order to form a malleable cement. The main GIC ingredients are commonly used in the form of an aqueous solution containing polymeric acid, and a finely divided glass powder, which are mixed by an appropriate method to form a viscous paste that sets rapidly. Alternative formulations wherein the components are distributed differently between the powder and aqueous phases are also commercially available, for example formulations wherein both the acid and the glass are present in the powder, and water is added to cause setting; or formulations in which some of the acid is blended with the glass powder and the rest is present in a solution in water. Generally, the components may commonly be used in a ratio of glass:polymeric acid:water of about 4:1:1 (by weight). Glass-ionomer cements can further contain a rheological modifier such as for example tartaric acid, which can be present in either the powder or the aqueous phase.

In an embodiment, the dental cement comprising lithium according to the invention is a glass ionomer cement (GIC) comprising lithium. Preferably, the GIC comprises a bioactive glass comprising lithium. More preferably, said bioactive glass is a bioactive glass comprising lithium as defined above.

In an embodiment the GIC comprises a glass component, a polymeric acid component, and water. The GIC may further comprise an optional rheological modifier.

The GIC may be prepared by mixing a precursor with an aqueous liquid. The components of the GIC may be distributed between the precursor and the liquid in different ways.

In an embodiment, the precursor comprises a glass component. In use this may be combined with a liquid comprising a polymeric acid component and water, in order to prepare a GIC. Either the precursor or the liquid may further comprise an optional rheological modifier.

In another embodiment, the precursor comprises a glass component and a polymeric acid component. In use this may be combined with a liquid comprising water, in order to prepare a GIC. Either the precursor or the liquid may further comprise an optional rheological modifier.

In an embodiment, the components may be used in the GIC in a ratio of glass component:polymeric acid component:water of about 4:1:1 by weight. For example, the components may be used in the GIC in a ratio of glass component:polymeric acid component:water of from 3 to 5: from 0.5 to 1.5: from 0.5 to 1.5 by weight.

In a preferred embodiment of the invention, the GIC or precursor thereof comprises a bioactive glass comprising lithium. In an embodiment, the GIC or precursor thereof comprises the bioactive glass in an amount of at least 0.1 wt %, at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, or at least 99 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

The GIC or precursor thereof comprises a glass component. Preferably said glass component comprises a bioactive glass comprising lithium. More preferably, the bioactive glass is a bioactive glass comprising lithium as defined above. The bioactive glass comprising lithium may form all or part of the glass component.

The GIC may suitably comprise other components in addition to the glass component.

The precursor of the GIC may comprise other components in addition to the glass component, or may consist of the glass component.

In an embodiment, the GIC or precursor thereof comprises a glass component in an amount of at least 1 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, or at least 95 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

In an embodiment, the bioactive glass comprising lithium forms at least part of the glass component of the GIC or precursor thereof. The glass component, or indeed the GIC or precursor as a whole, may, for example, comprise the bioactive glass in an amount of at least 0.1 wt %, at least 1 wt %, at least 2 wt %, at least 3 wt %, at least 4 wt %, at least 5 wt %, at least 6 wt %, at least 7 wt %, at least 8 wt %, at least 9 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, or at least 99 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

In some embodiments, it is preferred to use a high concentration of the bioactive glass comprising lithium. Suitably, the bioactive glass may be present in the glass component, or indeed in the GIC or precursor as a whole, in an amount of at least 10 wt %. For example, the glass component, or the GIC or precursor as a whole, may comprise the bioactive glass in an amount of at least 10 wt %, at least 11 wt %, at least 12 wt %, at least 13 wt %, at least 14 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, at least 95 wt %, or at least 99 wt %. Additionally or alternatively the glass component, or the GIC or precursor as a whole, may comprise the bioactive glass in an amount up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, or up to 15 wt %.

In addition to the bioactive glass comprising lithium, the glass component of the GIC or precursor thereof may further comprise other types of glass, e.g. aluminosilicate glasses such as fluoride-containing aluminosilicate glass. Such types of glass are well-known for dental applications, such as for example the glasses described in Sidhu, S. K. et al., J. Funct. Biomater. 2016, 7, 16; doi:10.3390/jfb7030016.

In another embodiment, the bioactive glass comprising lithium is the only glass in the GIC or precursor thereof. The glass component of the GIC or precursor thereof may consist of the bioactive glass comprising lithium.

Additionally or alternatively the glass component may be the sole glass component of the GIC or precursor thereof.

The inventors have found that it is possible to replace some or all of the glass in known commercial GICs, such as for example Ketac™ Cem radiopaque (3M), with the bioactive glass comprising lithium as defined above.

In an embodiment, the GIC or precursor thereof comprises the glass component in an amount of at least 1 wt %, at least 5 wt %, at least 10 wt %, at least 15 wt %, at least 20 wt %, at least 25 wt %, at least 30 wt %, at least 35 wt %, at least 40 wt %, at least 45 wt %, at least 50 wt %, at least 55 wt %, at least 60 wt %, at least 65 wt %, at least 70 wt %, at least 75 wt %, at least 80 wt %, at least 85 wt %, at least 90 wt %, or at least 95 wt %; and/or up to 100 wt %, up to 95 wt %, up to 90 wt %, up to 80 wt %, up to 70 wt %, up to 60 wt %, up to 50 wt %, up to 40 wt %, up to 30 wt %, up to 20 wt %, up to 15 wt %, or up to 10 wt %.

Preferably, the GIC comprises the glass component in an amount of at least 40 wt %, at least 45 wt %, at least 50 wt %, at least 55 wt %, at least 60 wt %, at least 65 wt %, at least 70 wt %, at least 75 wt %, or at least 80 wt %; and/or up to 90 wt %, up to 80 wt %, up to 70 wt %, up to 60 wt %, or up to 50 wt %. More preferably, the GIC comprises the glass component in an amount of from 50 wt % to 80 wt %, such as for example from 60 wt % to 70 wt %.

Suitably, the GIC precursor comprises the glass component in an amount of at least 50 wt %, at least 55 wt %, at least 60 wt %, at least 65 wt %, at least 70 wt %, at least 75 wt %, at least 80 wt %, at least 85 wt %, at least 90 wt %, or at least 95 wt %; and/or up to 100 wt %, up to 95 wt %, up to 90 wt %, up to 80 wt %, up to 70 wt %, or up to 60 wt %. More preferably, the GIC precursor comprises the glass component in an amount of from 50 wt % to 100 wt %, such as for example from 80 wt % to 90 wt %.

In an embodiment the GIC or precursor thereof comprises a polymeric acid component.

The polymeric acid component may comprise a poly (carboxylic acid), such as a for example poly(acrylic acid) (PAA), a copolymer of acrylic acid and maleic acid, poly (vinyl phosphonic acid), or any combination thereof.

In an embodiment, the GIC or precursor thereof comprises the polymeric acid component in an amount of at least 0.1 wt %, at least 1 wt %, at least 5 wt %, at least 10 wt %, at least 15 wt %, or at least 20 wt %; and/or up to 40 wt %, up to 30 wt %, up to 20 wt %, up to 15 wt %, up to 10 wt %, up to 1 wt %, or up to 0.1 wt %.

Preferably, the GIC comprises the polymeric acid component in an amount of at least 5 wt %, at least 10 wt %, or at least 15 wt %; and/or up to 30 wt %, up to 20 wt %, or up to 15 wt %. More preferably, the GIC comprises the polymeric acid component in an amount of from 5 wt % to 30 wt %, such as for example from 10 wt % to 20 wt %.

Suitably, the GIC precursor comprises the polymeric acid component in an amount of at least 0.1 wt %, at least 1 wt %, at least 5 wt %, at least 10 wt %, at least 15 wt %, or at least 20 wt %; and/or up to 40 wt %, up to 30 wt %, up to 20 wt %, up to 15 wt %, up to 10 wt %, up to 1 wt %, or up to 0.1 wt %.

The GIC may comprise water.

Suitably, the GIC comprises water in an amount of at least 0.1 wt %, at least 1 wt %, at least 5 wt %, at least 10 wt %, at least 15 wt %, or at least 20 wt %; and/or up to 40 wt %, up to 30 wt %, up to 20 wt %, up to 15 wt %, up to 10 wt %, up to 1 wt %, or up to 0.1 wt %.

In an embodiment, the GIC or precursor thereof further comprises an optional rheological modifier.

The rheological modifier may comprise an acid, such as for example tartaric acid, succinic acid, malic acid, maleic acid, itaconic acid, citraconic acid, ethylenediaminetetraacetic acid, propanetricarboxylic acid, citric acid, aconitic acid, salicylic acid, mellitic acid, or any combination thereof. Preferably, the rheological modifier comprises tartaric acid.

Preferably, the GIC or precursor thereof comprises the rheological modifier in an amount of from 0.01 wt %, from 0.1 wt %, from 0.25 wt %, or from 0.5 wt %; and/or up to 30 wt %, up to 25 wt %, up to 20 wt %, up to 15 wt %, up to 10 wt %, up to 7 wt %, up to 5 wt %, up to 3 wt %, or up to 1 wt %.

The GIC or precursor thereof may also comprise further optional ingredients. For example, bismuth oxide ($Bi_2O_3$) may be added as radio-opaque component.

The GIC or precursor thereof may further comprise adjuvants such as such as pigments, viscosity modifiers, wetting agents, milling agents, extending fillers, radiopacifiers, and/or metal powders (e.g. silver or silver alloys).

The dental filling material of the invention (which may for example be a GIC) may take any suitable form. Suitably, the dental filling material may be in a ready-to-use form. Conveniently, the dental filling material may be in the form of a paste.

The invention also embraces a precursor of the dental filling material.

The precursor requires the addition of one or more further components to make the dental filling material ready for use.

The precursor of the dental filling material may comprise a solid, for example a particulate solid.

The precursor may be dry, i.e. require the addition of a liquid before use. The precursor may, for example, comprise or consist of a powder.

Advantageously, the precursor may allow the dental filling material to be formed on addition of a liquid. Advantageously, no addition of any other solid may be required.

Suitably, the precursor may comprise or consist of the entirety of a solid component of the dental filling material.

The precursor may advantageously be provided in unitary form, for example from a single receptacle or storage container. Alternatively, the precursor may comprise multiple parts to be combined, for example from separate receptacles or storage containers.

The precursor may be combined with a liquid.

Advantageously, the precursor may be provided in the form of a capsule, which capsule further comprises a liquid. The precursor and the liquid, therefore, can be packaged together in a capsule.

The liquid may for example comprise an acid and/or water.

In an embodiment, the liquid comprises an acid.

Examples of suitable acids include tartaric acid, succinic acid, malic acid, maleic acid, itaconic acid, citraconic acid, ethylenediaminetetraacetic acid, propanetricarboxylic acid, citric acid, aconitic acid, salicylic acid and/or mellitic acid. Preferably, the liquid comprises the acid in an amount of from 1 wt %; and/or up to 20 wt %, up to 10 wt %, up to 7 wt %, up to 5 wt %, up to 3 wt %, or up to 1 wt %.

Advantageously, the liquid may comprise or consist of an aqueous acid, for example an aqueous form of one or more of the acids listed above.

In an embodiment, the liquid comprises water. Preferably, the liquid comprises water in an amount of from 70 wt %, from 80 wt %, from 90 wt %, or from 95 wt %; and or up to 100 wt %, up to 99 wt %, up to 95 wt %, or up to 90 wt %.

In an embodiment, the precursor may be a GIC precursor as defined above. A GIC may be prepared by mixing the GIC precursor with an aqueous liquid. The components of the GIC may be distributed between the GIC precursor and the liquid in different ways. In an embodiment, the GIC precursor comprises a glass component as defined above. In use this may be combined with a liquid comprising a polymeric acid component as defined above and water, in order to prepare a GIC. Either the precursor or the liquid may further comprise an optional rheological modifier as defined above. In another embodiment, the GIC precursor comprises a glass component as defined above and a polymeric acid component as defined above. In use this may be combined with a liquid comprising water, in order to prepare a GIC. Either the precursor or the liquid may further comprise an optional rheological modifier as defined above.

The liquid may advantageously be provided in unitary form, for example from a single receptacle or storage container. Alternatively, the liquid may comprise multiple parts to be combined, for example from separate receptacles or storage containers.

A precursor can be used by a dentist or dental surgeon to prepare the dental filling material in situ when performing a dental repair procedure. Combining a precursor with a liquid may form a paste, which can be placed in a tooth cavity and shaped as required. The material can then be allowed to set over time or cured, for example with the assistance of UV light, resulting in a hard filling.

In an embodiment of the invention, the dental filling material is obtainable by mixing a precursor of the dental filling material and a liquid. Preferably, the precursor is as defined above and/or the liquid is as defined above.

An aspect of the invention provides a method of repairing dentine or treating damage to dentine, which comprises administering to a patient in need thereof a dental filling material or precursor thereof in accordance with any aspect or embodiment of the invention.

In an embodiment, the method comprises treating a dental lesion wherein the pulp is not exposed. Preferably, the method comprises treating a dental lesion wherein dentine is exposed but the pulp is not exposed.

The following non-limiting examples are provided by way of illustration only.

EXAMPLES

Abbreviations

"BG" stands for bioactive glass or bioactive glasses.

"45S5" or "45S5 BG" stands for a bioactive glass composed of 45 wt % $SiO_2$, 24.5 wt % CaO, 6.0 wt % $P_2O_5$ and 24.5 wt % $Na_2O$; corresponding to 46.1 mole % $SiO_2$, 26.9 mole % CaO, 2.6 mole % $P_2O_5$ and 24.4 mole % $Na_2O$.

"LithGlass" stands for a bioactive glass composed of 46.1 mole % $SiO_2$, 26.9 mole % CaO, 2.6 mole % $P_2O_5$ and 24.4 mole % $Li_2O$.

The expression "Li" followed by a number from 0 to 100, e.g. "Li100", stands for a bioactive glass composed of 46.1 mole % $SiO_2$, 26.9 mole % CaO and 2.6 mole % $P_2O_5$, and 24.4 mole % $Li_2O$ and/or $Na_2O$. The number from 0 to 100 indicates the molar percentage of $Li_2O$ in the fraction made up by $Li_2O$ and/or $Na_2O$. For example, if the bioactive glass contains only $Li_2O$ and no $Na_2O$, the number is 100 and the bioactive glass is indicated as "Li100"; if the bioactive glass contains only $Na_2O$ and no $Li_2O$, the number is 0 and the bioactive glass is indicated as "Li0". "Li0" can be used interchangeably with "45S5". "Li100" can be used interchangeably with "LithGlass".

"GIC" stands for glass ionomer cement or glass ionomer cements, unless otherwise indicated.

"LithGlassGIC" denotes glass ionomer cement(s) containing Li100 (LithGlass).

"Li0GIC" denotes glass ionomer cement(s) containing Li0 (45S5).

"Ketac™ Cem radiopaque" is a commercial glass ionomer cement obtainable from 3M.

"Dycal" is a commercial pulp capping material containing calcium hydroxide obtainable from Dentsply.

Materials and Methods

Bioactive Glass (BG) Synthesis

Bioactive glasses were formed using a melt quench route. We created either conventional 45S5 BG or substituted $Li_2O$ for $Na_2O$ in 45S5 BG on a molar basis (Table 1). Glass components were melted in a platinum crucible at 1250° C. for 1 h, then at 1350° C. for an additional hour before being rapidly quenched in water. Glass frits were then crushed in a steel mortar, milled and to sieved to create particles of <38 μm in diameter.

TABLE 1

| Glass compositions (mol %) | | | | | |
| --- | --- | --- | --- | --- | --- |
| Bioactive glasses | $SiO_2$ | $P_2O_5$ | CaO | $Na_2O$ | $Li_2O$ |
| Li0 (45S5) | 46.1 | 2.6 | 26.9 | 24.4 | — |
| Li100 (LithGlass) | 46.1 | 2.6 | 26.9 | — | 24.4 |

Glass Ionomer Cement (GIC) Formation

Glass ionomer cements were formed by replacing part of the powder component of the commercial GIC Ketac™ Cem radiopaque (3M ESPE Henry Schein Medical) with Li100 (LithGlass) or Li0 (45S5) as outlined in Table 2.

TABLE 2

| Amount of Li0/Li100 and commercial GIC powder in powder compositions | | |
| --- | --- | --- |
| | Li0/Li100 (g) | Ketac™ Cem Radiopaque (g) |
| 10% Li0GIC | 1 Li0 | 9 |
| 10% LithGlassGIC | 0.873 Li100 | 9.126 |
| 15% LithGlassGIC | 1.310 Li100 | 8.690 |
| 20% LithGlassGIC | 1.746 Li100 | 8.254 |
| 25% LithGlassGIC | 2.183 Li100 | 7.817 |
| 30% LithGlassGIC | 2.619 Li100 | 7.381 |
| 40% LithGlassGIC | 3.492 Li100 | 6.508 |

For the avoidance of doubt, the percentages in the left-hand column of Table 2 denote the weight percent of the powder component of the original commercial GIC (Ketac™ Cem radiopaque) that has been replaced with Li0 (45S5) or its molar equivalent of Li100: where Li100 is used, the molar amount of $Na_2O$ in that weight percent of 45S5 has been replaced with the same molar amount of $Li_2O$ in the Li100. In order to do this, the mass of the substituted bioglass was adjusted according to Table 2, to account for the differences in the atomic weights of lithium and sodium (lithium has a lower atomic weight than sodium).

Cements were formed in pre-sterilised polyurethane moulds by mixing each powder composition listed in Table 2 above with the liquid component of the commercial GIC Ketac™ Cem radiopaque. The following table (Table 3) shows the masses and volumes of powder and liquid that were used. In Table 3 "GIC" stands for Ketac™ Cem radiopaque.

TABLE 3

| Material | Powder (mg) | Liquid (μl) |
| --- | --- | --- |
| GIC (Ketac ™ Cem radiopaque) | 315 | 50 |
| 10% Li0GIC | 315 | 80 |
| 10% LithGlassGIC | 315 | 80 |
| 15% LithGlassGIC | 315 | 85 |
| 20% LithGlassGIC | 315 | 90 |
| 25% LithGlassGIC | 315 | 95 |
| 30% LithGlassGIC | 315 | 100 |
| 40% LithGlassGIC | 315 | 110 |

The cements were allowed to set for 1 h at 37° C. Resulting cements were ~6 mm in diameter and ~6 mm in height.

Cytotoxicity Assay Based on ISO10993:5

The cytotoxicity of LithGlassGIC, Li0GIC and Ketac™ Cem radiopaque were assessed using a modified version of ISO10993:5. The positive control material consisted of an organo-tin-stabilised polyvinyl chloride (PVC) sheet. Non-toxic MED7536 noDrop tubing was used as the negative control (both materials from Raumedic AG, Helmbrechts, Germany). Control materials were sterilised with 70% ethanol for 1 h, washed with phosphate buffered saline (PBS), and then soaked in alpha minimum essential medium (αMEM) for 7 days at 37° C., using a surface area to volume ratio of 3 $cm^2$/mL. Cements were soaked in αMEM at a surface area to volume ratio of 3 $cm^2$/mL for (15, 30) minutes, (1, 2, 4, 8, 12) hours, and (1,3,7) days to create conditioned media. Mouse dental pulp cells 17IA4 were plated in 96-well plates at 20,000 cells/$cm^2$ and incubated (37° C., 5% $CO_2$/95% air, 100% humidity) for 24 h in αMEM with L-Glutamine supplemented with 10% (v/v) foetal bovine serum (FBS) and 1% (v/v) antibiotic-antimycotic. Medium was then replaced with cement-conditioned (LithGlassGIC) or control medium and cells incubated for another 24 h. To measure cell metabolic activity, 20 μl of a 5 mg/ml solution of MTT (3-(4,5-Dimethylthiazol-2-yl)-2, 5-diphenyltetrazolium bromide, Sigma) in PBS was added to the media and incubated for 4 h. After removing the solution from each well, the resulting product was dissolved in 200 μl of dimethyl sulfoxide. Absorbance was then read on a colorimetric plate reader (Thermo Multiskan Ascent 354 microplate reader) at 540 nm with background subtraction at 630 nm.

Mouse Molar Injury

All animals used in this study were handled in accordance with UK Home Office Regulations (project license 70/7866 and personal license ID4E60F01), which was approved by the King's College London animal ethics committee and complies with ARRIVE guidelines. Experimental procedures were approved by the King's College London Ethical Review Process.

Figure 6:
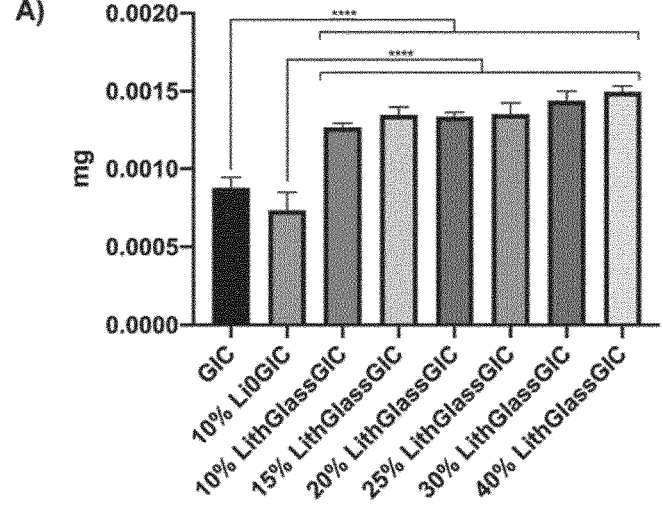
FIG. 6 shows: A) Mineral formation analysis by microCT at the injury site after 4 weeks of the molars capped with Dycal with Ketac™ Cem radiopaque (indicated as "GIC"), 10% Li0GIC, 10%, 15%, 20%, 25%, 30% or 40% LithGlassGIC. B) Histology of reactionary dentin formation after 4 and 6 weeks of the molars capped with Dycal with Ketac™ Cem radiopaque (indicated as "GIC"), 10% Li0GIC, 10%, 15%, 20%, 25%, 30% or 40% LithGlassGIC.
Figure 6:
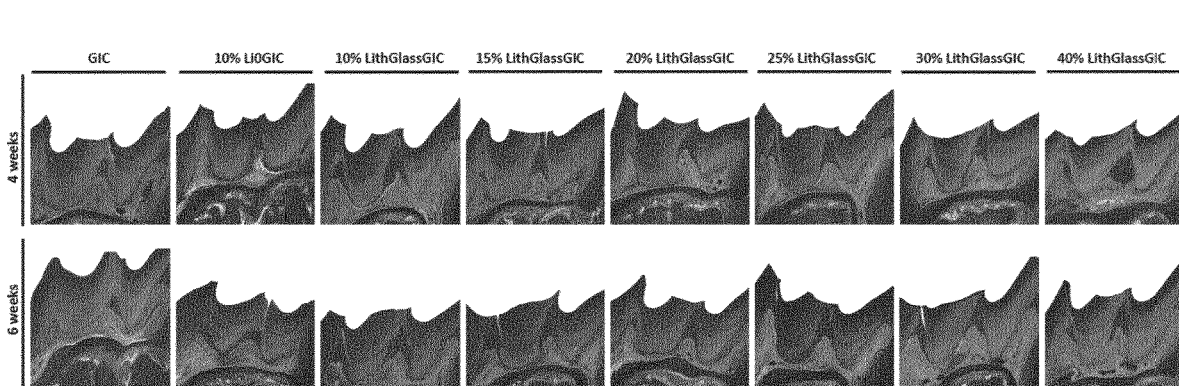
Figure 8:
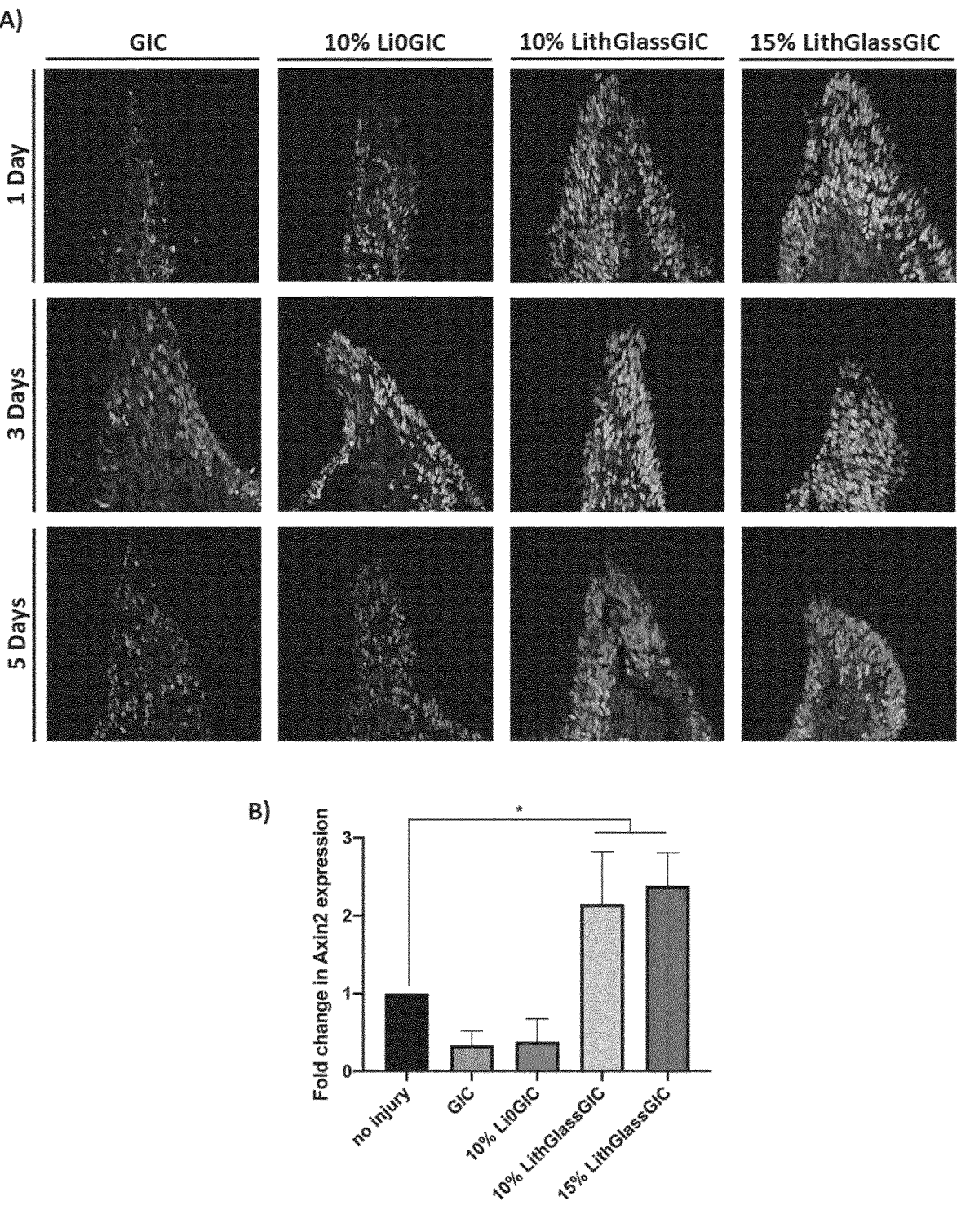
FIG. 8 shows: A) Wnt-responsive cells (green) counterstained with DAPI (blue) in molars 1, 3 and 5 days after injuries were capped with Ketac™ Cem radiopaque (indicated as "GIC"), 10% LiOGIC, 10% LithGlassGIC or 15% LithGlassGIC (n=6 per time point). All teeth were drilled in TCF/Lef:H2B-GFP reporter mice. Images show 63× magnification of sagittal sections. B) Axing expression of dental pulp cells collected either without injury or after one day of injury and capping with Ketac™ Cem radiopaque (indicated as "GIC"), 10% LiOGIC, 10% LithGlassGIC or 15% LithGlassGIC. (n=6) (*P<0.05).

Six-week-old CD1 wild-type mice and TCF/Lef:H2B-GFP reporter mice were used in this study. The mice were anesthetized intraperitoneally with a solution containing Hypnorm (fentanyl/fluanisone; VetaPharma Ltd.), sterile water, and Hypnovel (midazolam; Roche) in a 1:2:1 ratio, at a rate of 10 ml/kg. Two upper first molars were drilled using a rounded carbide burr FG ¼ with a high-speed hand piece. The drilling was from the occlusal surface to the superficial layer of dentin and was capped with GIC compositions, as indicated in FIGS. 6 and 8, or with calcium hydroxide Dycal (Dentsply, 623801). CD1 mice were sacrificed after 4 and 6 weeks. TCF/Lef:H2B-GFP reporter mice were sacrificed after 1, 3 and 5 days. A total of 36 TCF/Lef:H2B-GFP reporter mice (72 damaged molars) and 24 CD1 mice (48 molars) were used.

Saliva and Blood Collection

Two upper first molars of 6-week-old CD1 wild-type mice were drilled as mentioned in the "Mouse molar injury" section above, and filled with 10% or 40% LithGlassGIC. After 4 and 24 h, mice were anesthetised intraperitoneally as above and saliva production stimulated by an intraperitoneal injection of pilocarpine (0.5 mg/kg). Mice were positioned on their backs with their heads slightly down and after 12 min saliva was collected for 10 min by plastic syringe. For blood collection, the anesthetised mice were placed on their back and blood collected from their heart using a cardiac puncture technique. 500 µl of blood was collected per mouse and placed in a sodium heparin anticoagulant tube. Mice were sacrificed after saliva and blood collection. 15 mice were used for saliva and blood collection.

Pulp Collection

The upper first molars of CD1 wild-type mice were drilled as mentioned in the "Mouse molar injury" section above, and filled with either 10% and 15% LithGlassGIC, 10% LiOGIC or Dycal and capped with Ketac™ Cem radiopaque. Teeth without injury were used as controls. After 1 day, 21 G needles were used as an elevator to extract teeth from the alveolar bone and placed in ice cold PBS. To visualise the pulp chamber, teeth were separated at the crown-root junction using a 23 scalpel blade. The pulp was gently scraped from the pulp chamber and root canal using 0.6 mm straight tip forceps. The pulp was then placed into cold RNAlater (AM7020, Thermo Fisher Scientific) and stored at −80° C. A total of 30 CD1 mice were used.

Elemental Analysis by Inductively Coupled Plasma Mass Spectroscopy (ICP-MS)

ICP-MS was performed to measure the concentration of lithium, silicon, aluminium, calcium and phosphorus in cell culture media and biological fluids. 0.4 ml of blood from each animal was digested in 2 ml 100% nitric acid ($HNO_3$) at 50° C. overnight and then diluted with 7.6 ml sterile water. Digested blood, saliva and media were diluted 1:100 in 1% nitric acid and analysed on a Perkin Elmer NexION 350D with a CETAC AX520 autosampler using customary calibration standards. Syngistix software was used to analyse the data.

Quantitative Polymerase Chain Reaction

RNA was extracted from the dental pulp using TRIzol (Thermo Fisher Scientific) as recommended by the manufacturer. RNA was quantified by Nanodrop and then revered transcribed into cDNA. Each well contained 10 µl of solution, of which 5 µl was syber green (KAPA SYPER® fast qPCR kits), 0.1 µl forward primer, 0.1 µl reverse primer and 4.8 µl cDNA. The study was performed in triplicate and BioRad and Kappa Syber Fast (Kappa Biosystems) software were used for quantitative analysis. Beta-actin was used as housekeeping gene (Forward-GGCTGTATTCCCCTC-CATCG (SEQ ID NO:1), Reverse-CCAGTTGGTAACAATGCCATGT (SEQ ID NO:2)) and Axing was the readout for Wnt/β-catenin activity (Forward-TGACTCTCCTTCCAGATCCCA (SEQ ID NO:3), Reverse-TGCCCACACTAGGCTGACA (SEQ ID NO:4)). Data were analysed using the ∆∆CT method.

Immunofluorescence Staining

Teeth extracted from TCF/Lef:H2B-GFP reporter mice were decalcified in 19% ethylenediaminetetraacetic acid (EDTA) in $H_2O$ and then immersed in 30% sucrose/PBS overnight at 4° C. Teeth were embedded in optimal cutting temperature (OCT) using dry ice and ethanol. 12 µm sections were cut and incubated with chicken polyclonal anti-green fluorescent protein (anti-GFP) antibody (1:2000; Abcam; ab13970) overnight at 4° C. Sections were washed and incubated with secondary antibody (1:500; Thermo Fisher Scientific; A21449) for 1 h at room temperature.

Histological Staining

Molar teeth were decalcified in 19% EDTA (pH 6) for 4 weeks. Teeth were embedded in wax blocks and sectioned (8 µm) using a microtome (LEICA) onto SuperfrostPlus® glass slides (J1800AMNZ, Thermo Fisher Scientific). Sections were stained using Masson's Trichome.

Micro Computer Tomography (CT) Scanning and Mineral Analysis

Molar teeth were dissected after 4 weeks and fixed with 4% (w/v) paraformaldehyde (PFA) for 24 h at 4° C. and then placed in PBS.

Teeth were scanned using a Locus SP micro-computed tomography scanner (Bruker Skyscan 1272). MicroView software (GE Healthcare) was used for visualisation and analysis. Two-dimensional images were obtained from µCT cross-sectional images of the upper first molar to evaluate mineral formation. The region of interest was set as a standard for all teeth and mineral analysis performed using an ROI of X=0.2 mm, Y=0.4 mm and Z=0.2 mm. The region measured comprised only the injury site. The complete ROI filled with mineral was 0.0017 mg.

Teeth were also scanned using a Scanco µCT50 micro-computed tomography scanner. Teeth were fixed firmly in 6 mm scanning tube using cotton gauze. The microCT manufacture provided the calibration objects which can be automatically scaled the scans at reconstruction including 5 rods of hydroxyapatite (HA) at concentration of 0 to 790 mg $HA/cm^3$ and the absorption values expressed in Hounsfield units (HU). MicroView software (Parallax Innovations) was used for visualisation and analysis. Two-dimensional images (2D) were obtained from microCT cross-sectional images of the drilled upper first molar to evaluate mineral formation. The line function of the software was used to measure the dentin thickness from the top of the middle pulp horn to the point where the dentin was drilled. The advanced region of interest (ROI) spline function was set as a standard for all teeth (ROI X=0.2 mm, Y=0.4 mm and Z=0.2 mm) to measure the mineral content. Standardised contrast setting were set to window/level values of 23000/18000. Auto threshold was selected and water was set at −1000 HU and bone density (HA) at 5343 HU. Mineral analysis was performed to assess the area under the damage site. The complete ROI filled with mineral was 0.0017 mg.

Statistical Analysis

The data are presented as means and standard deviations. Data represent at least three independent experiments. A one-way ANOVA followed by a post-hoc Tukey test were used for statistical analysis (p<0.05). Methods conform with STROBE guidelines.

Results and Discussion

We created 45S5 BG in which all of the sodium had been replaced with lithium on a molar basis (LithGlass) (Brauer et al., 2016, Bruckner et al., 2016). We then formed cements by substituting part (10-40%) of the powder phase of the commercial GIC Ketac™ Cem radiopaque with LithGlass to form LithGlassGIC. All compositions of LithGlassGIC had mixing properties similar to those of the unmodified commercial cement. All set quickly and visually formed hard cements for both in vitro and in vivo studies.

To assess the release of ions from LithGlassGIC, we placed cements in cell culture media for up to 7 days and assessed ion release by ICP-MS (FIG. 5a-e). The concentration of calcium and phosphorus in cell culture medium varied as expected and in line with previous in vitro observations (da Silva et al., 2017). Increasing the fraction of the powder phase of the commercial GIC with LithGlass resulted in expected increases in silicon concentrations and decreases in aluminium concentrations, in line with the substitution of a silicon-rich BG for an aluminosilicate glass.

Analysis of lithium concentrations indicated that with increasing substitution of LithGlass into GIC, more lithium was released into the cell culture medium. However, whereas at low levels of substitution (10-15% LithGlass), lithium concentrations in the cell culture medium increased as expected, for higher levels of substitution (20-40%), lithium levels plateaued, suggesting a solubility limit for lithium in cell culture medium in the range of 2000-3000 ppm. In all cases, lithium was released quickly, reaching a peak within ~12 h, after which concentrations stayed relatively stable for all formulations for 7 days.

Figure 5:
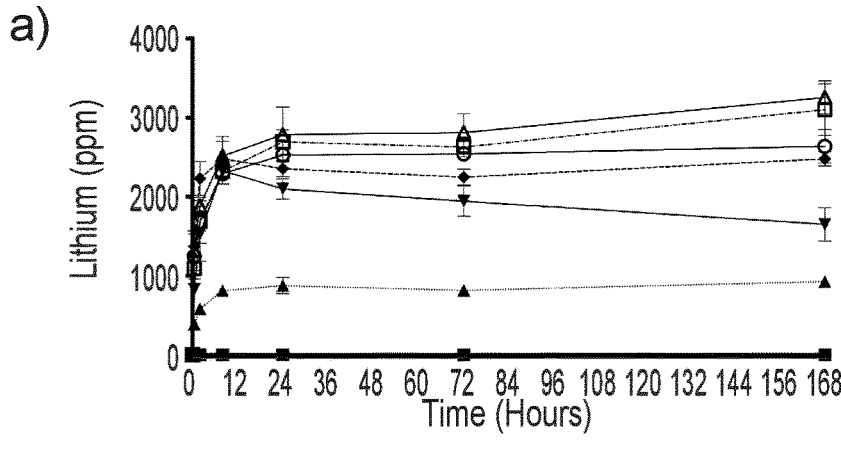
FIG. 5 shows: Elemental concentrations of a) lithium, b) silicon, c) calcium, d) phosphorus and e) aluminium in dissolution ion medium created by Ketac™ Cem radiopaque (indicated as "GIC"), 10% Li0GIC and different formulations of LithGlassGIC in cell culture media. f) Normalised metabolic activity of 17IA4 cells after 24 h treatment with dissolution ions formed from soaking Ketac™ Cem radiopaque (indicated as "GIC"), 10% Li0GIC and different formulations of LithGlassGIC in cell culture media. (P<0.0001).
Figure 5:
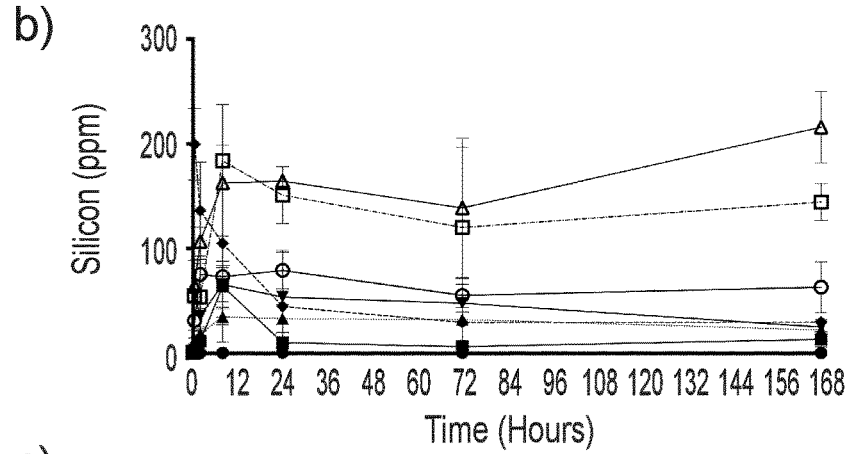
Figure 5:
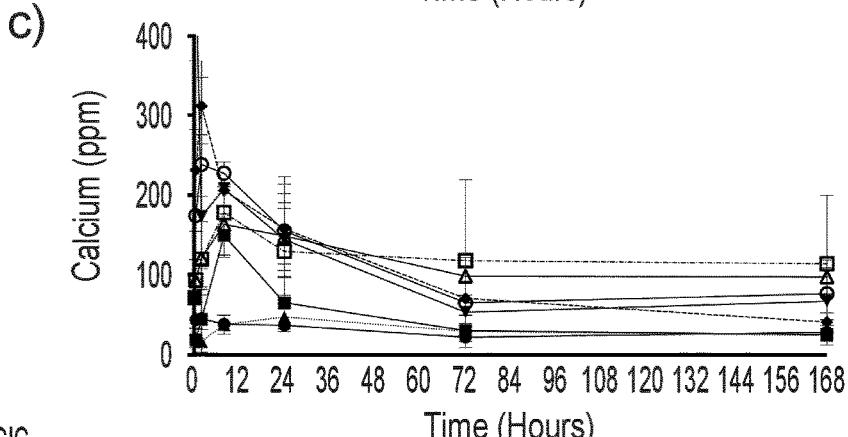

We next tested the viability of dental pulp cells after exposure to the dissolution products of LithGlassGIC, according to a modified version of ISO10993:5. Viability was compared to that of cells exposed to 10% Li0GIC and Ketac™ Cem radiopaque, as well as known toxic (tin-stabilised PVC) and non-toxic polymer controls. The normalised MTT activity of 17IA4 mouse dental pulp cells treated with 10%, 15%, 20%, 25%, 30% and 40% Lith-GlassGIC was significantly lower than that of negative controls, but no different than that of positive controls (FIG. 5f). These findings were similar to those of Ketac™ Cem radiopaque and 10% Li0GIC, both of which were similarly toxic to cells. These finding show that like Ketac™ Cem radiopaque, LithGlassGIC are toxic to cells in ISO10993:5 tests and should not be used in cases in which the dental pulp is exposed. However, they also suggest that, like commercial GIC, LithGlassGIC may have applications in injuries when the pulp is not exposed, but rather protected by a (thin) layer of dentin.

Figure 9:
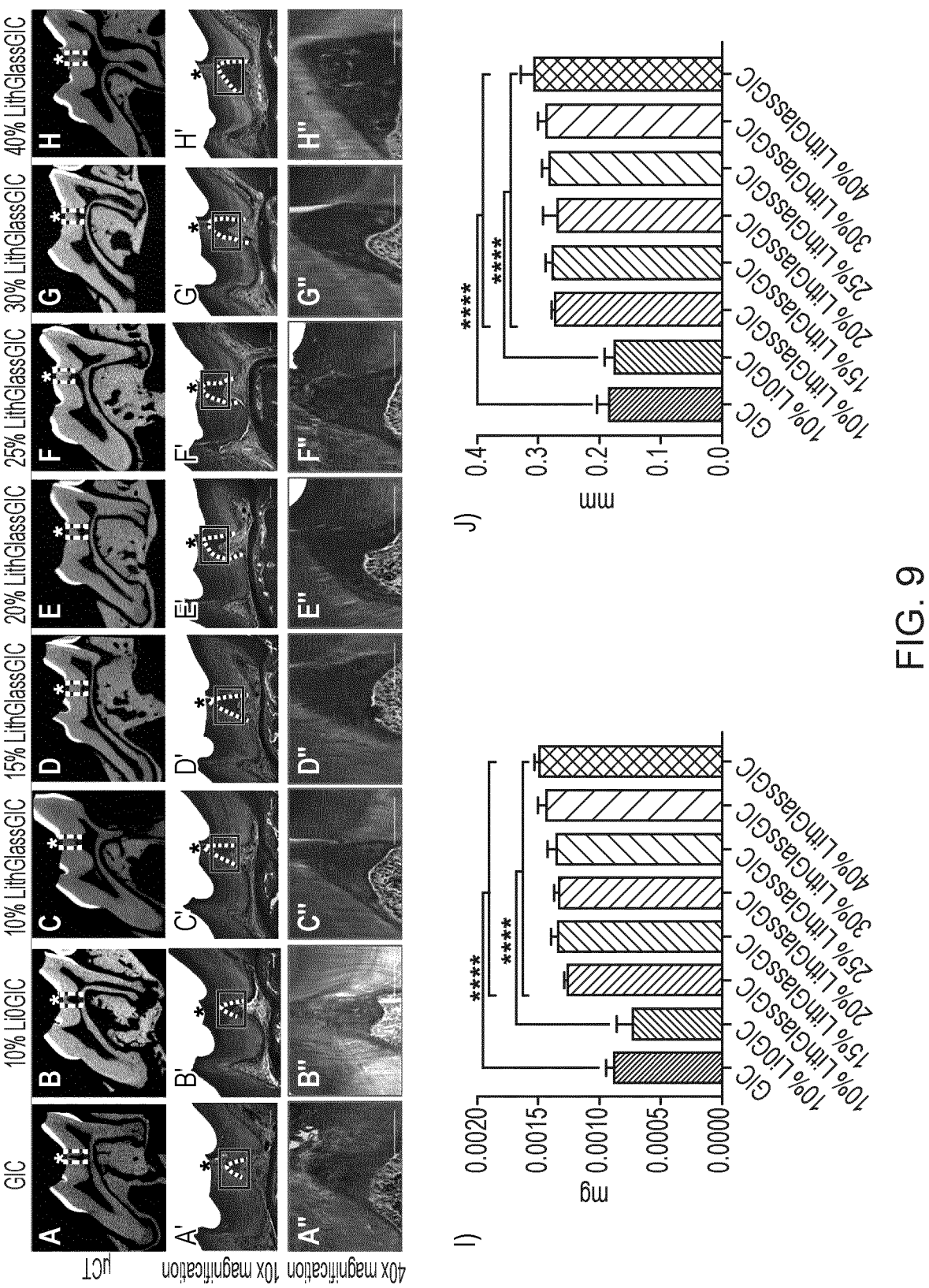
FIG. 9 shows.

We investigated whether in non-exposed pulp, lithium ions released from a GIC would still be able to stimulate dentine repair. Therefore, we created a defect model in murine molars using a dental burr to drill the hole that left a thin layer of dentine above the pulp and capped the defects with Ketac™ Cem radiopaque, 10% Li0GIC, or a range of formulations of LithGlassGIC. Mice were sacrificed after 4 or 6 weeks and microCT and histochemical analyses performed. MicroCT analyses, which allowed us to visualise and quantify mineral deposition at the drill site, showed that with increasing substitution of LithGlass into the GIC, the total volume of mineral in the defect site increased (FIG. 6A and FIGS. 9A-H and 9I). Moreover, microCT linear measurements showed a thicker dentin band was found with increasing substitution of LithGlass into the GIC (FIG. 9J). In all cases the total volume of mineral was significantly larger (more mineralised tissue and higher dentin thickness) in LithGlassGIC conditions compared to Ketac™ Cem radiopaque and 10% Li0GIC. We then analysed the repair by histology and found that more reactionary dentin was visible in teeth treated with LithGlassGIC (FIG. 6B and FIG. 9A'-H'). Moreover, in LithGlassGIC-treated teeth, we observed that with increasing substitution of LithGlass in the GIC, we could restore the thickness of the dentin bridge better on the pulp side compared to the controls. These observations confirm that more reactionary dentin is formed after placement of LithGlassGIC than is observed in non-lithium containing GIC cappings.

Figure 7:
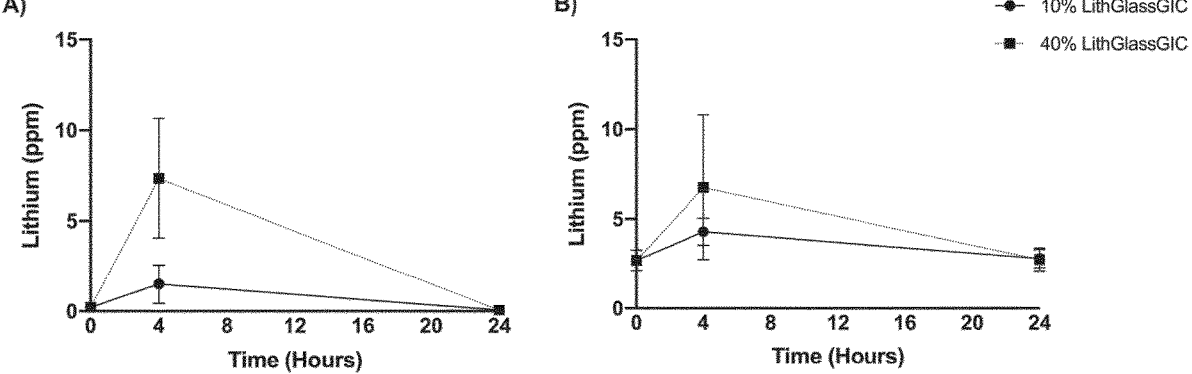
FIG. 7 shows: A) Lithium concentration in mouse saliva 4 and 24 hours after placing 10% and 40% LithGlassGIC in the upper $1^{st}$ molars of teeth. B) Lithium concentration in mouse blood 4 and 24 hours after placing 10% and 40% LithGlassGIC in the upper $1^{st}$ molars teeth. Two upper first molars teeth in CD1 wild-type mice were used. 5 mice were used per each time points. Time 0 shows lithium concentration in blood and saliva, collected from untreated mice (n=5).

To understand if substitution of LithGlass into GIC was safe, we next assessed the levels of lithium in blood and saliva after repairing molar defects with LithGlassGIC. 4 h after placing 10% and 40% LithGlassGIC, lithium levels in the range of 4-7 ppm were detected in the blood and between 2 and 8 ppm in the saliva (FIG. 7A/B). Lithium concentrations in saliva were significantly higher (p<0.01) after 4 h in animals treated with 40% LithGlassGIC compared to 10% LithGlassGIC; however, blood levels remained within the safe therapeutic range established for patients on lithium therapies (4.2-8.3 ppm) (CHEN et al., 2004, Severus et al., 2008, Cipriani et al., 2013). 24 h after placing 10% or 40% LithGlassGIC, blood and saliva levels were no different than those at baseline (time 0) (p>0.05). This suggests that dental treatments with LithGlassGIC yield low levels of lithium in both local and systemic fluids. Moreover, they suggest that immediately upon application, a burst of lithium is released from LithGlassGIC that is then quickly cleared by the body. Further release of lithium is at undetectable levels. Taken together, these data suggest that systemic lithium release from LithGlassGIC is minimal and results in safe levels in the body that are quickly cleared.

Finally, to understand if LithGlassGIC stimulated tertiary dentine formation by regulating Wnt/β-catenin activity in dental pulp cells, we used TCF/Lef:H2BGFP mice in which Wnt active cells express green fluorescent protein (GFP). We carried out the same injury model described above and then capped molars with either Ketac™ Cem radiopaque, 10% Li0GIC or 10 or 15% LithGlassGIC and sacrificed mice after 1, 3 or 5 days. Immunofluorescence analyses showed pronounced positive GFP staining in TCF/Lef:H2B-GFP reporter mice that received capping with either 10% LithGlassGIC or 15% LithGlassGIC (FIG. 8A). This showed a positive effect of LithGlassGIC on Wnt activity especially after one day post damage. Mice treated with standard Ketac™ Cem radiopaque or 10% Li0GIC showed little positive staining for GFP. To confirm these results, we repeated the experiment in wild type mice and extracted the tooth pulp after 1 day. Expression levels of the Wnt/β-catenin reporter Axin2 were significantly higher in dental pulp cells exposed to 10% and 15% LithGlassGIC compared to uninjured molars; however, treatment with Ketac™ Cem radiopaque or 10% Li0GIC had no significant effect (FIG. 8B).

In this study, lithium was released quickly into cell culture media when soaked with 10%-40% LithGlassGIC, achieving concentrations that are known to upregulate Wnt signalling (da Silva et al., 2017). Without wishing to be bound by theory, the fast release of lithium from LithGlassGIC is believed to be important to upregulate Wnt signalling immediately after placing the cement in the cavity. A standard ISO10993:5 test was performed to measure metabolic activity in cells exposed to the dissolution products of Lith-GlassGIC. Lithium concentrations released from Lith-GLassGIC were higher than those reported to be toxic (~700 ppm) (Tylkowski et al., 2013) which may have contributed to their toxicity. However, the toxicity of LithGlassGIC was not significantly different from that of 10% Li0GIC (no lithium-releasing cement). Without wishing to be bound by theory, this is believed to show that factors released from the cements other than lithium are likely responsible for cell toxicity.

In our non-exposed pulp cavity model, LithGlassGIC was applied to murine upper first molars. We observed higher localised mineralization and thicker mineral bands in teeth treated with LithGlassGIC compared to controls. Indeed, the distance from the point where the dentin was drilled to the top of the middle pulp horn was significantly smaller when teeth were capped with GIC or 10% Li0GIC compared with teeth treated with LithGlassGIC (0.25-0.29 mm). Our findings confirm that LithGlassGIC enhanced the formation of reactionary dentin which gives more protection for the tooth.

In this study, Wnt reporter mice TCF/Lef:H2BGFP and Axin2 expression assays were able to demonstrate that lithium levels released from LithGlassGIC cements are sufficient to promote intracellular Wnt activity at early time points. It was reported that a significant elevation of Wnt responsive cells occurred 3 days post damage and new odontoblasts-like cells are detected 5 days post damage. In this study, Axin2 was highly expressed in dental pulp cells one day after teeth were treated with LithGlassGIC compared to treatment with controls cements or intact teeth. These findings confirm that lithium released quickly from LithGlassGIC and penetrated through the dentin to the dental pulp.

Taken together, these observations confirm that LithGlassGIC quickly releases lithium, stimulates Wnt/β-catenin activity, and enhances tertiary dentine formation in pulp cells in a murine molar damage model that does not expose the dental pulp. The levels of lithium released from LithGlassGIC are similar to therapeutic levels known to be safely tolerated in humans. Therefore, LithGlassGIC may find use in a range of therapeutic applications to stimulate tertiary dentine formation to repair tooth defects.

REFERENCES

ANGELOVA, A. V., ZAUGG, L. K., NEVES, V., LIU, Y. & SHARPE, P. T. 2018. Tooth Repair and Regeneration. *Current oral health reports,* 5, 295-303.

BAUER, M., ALDA, M., PRILLER, J. & YOUNG, L. 2003a. Implications of the neuroprotective effects of lithium for the treatment of bipolar and neurodegenerative disorders. *Pharmacopsychiatry,* 36, 250-254.

BAUER, M., FORSTHOFF, A., BAETHGE, C., ADLI, M., BERGHÖFER, A., DÖPFMER, S. & BSCHOR, T. 2003b. Lithium augmentation therapy in refractory depression—update 2002. *European archives of psychiatry and clinical neuroscience,* 253, 132-139.

BRAUER, D. S. 2015. Bioactive glasses—structure and properties. *Angewandte Chemie International Edition,* 54, 4160-4181.

BRAUER, D. S., BRÜCKNER, R., TYLKOWSKI, M. & HUPA, L. 2016. Sodium-free mixed alkali bioactive glasses. *Biomedical glasses,* 2.

BRAUER, D. S., GENTLEMAN, E., FARRAR, D. F., STEVENS, M. M. & HILL, R. G. 2011. Benefits and drawbacks of zinc in glass ionomer bone cements. *Biomedical Materials,* 6, 045007.

BRÜCKNER, R., TYLKOWSKI, M., HUPA, L. & BRAUER, D. S. 2016. Controlling the ion release from mixed alkali bioactive glasses by varying modifier ionic radii and molar volume. *Journal of Materials Chemistry* B, 4, 3121-3134.

CHEN, K. P., SHEN, W. W. & LU, M. L. 2004. Implication of serum concentration monitoring in patients with lithium intoxication. *Psychiatry and clinical Neurosciences,* 58, 25-29.

CIPRIANI, A., HAWTON, K., STOCKTON, S. & GEDDES, J. R. 2013. Lithium in the prevention of suicide in mood disorders: updated systematic review and meta-analysis. *Bmj,* 346, f3646.

CLÉMENT-LACROIX, P., Al, M., MORVAN, F., ROMAN-ROMAN, S., VAYSSIÈRE, B., BELLEVILLE, C., ESTRERA, K., WARMAN, M. L., BARON, R. & RAWADI, G. 2005. Lrp5-independent activation of Wnt signaling by lithium chloride increases bone formation and bone mass in mice. *Proceedings of the National Academy of Sciences,* 102, 17406-17411.

CRISP, S., PRINGUER, M. A., WARDLEWORTH, D. & WILSON, A. D. 1974. Reactions in glass ionomer cements: II. An infrared spectroscopic study. *Journal of dental research,* 53, 1414-1419.

DA SILVA, J. G., BABB, R., SALZLECHNER, C., SHARPE, P. T., BRAUER, D. S. & GENTLEMAN, E. 2017. Optimisation of lithium-substituted bioactive glasses to tailor cell response for hard tissue repair. *Journal of materials science,* 52, 8832-8844.

DEL SER, T., STEINWACHS, K. C., GERTZ, H. J., ANDRES, M. V., GOMEZ-CARRILLO, B., MEDINA, M., VERICAT, J. A., REDONDO, P., FLEET, D. & LEON, T. 2013. Treatment of Alzheimer's disease with the GSK-3 inhibitor tideglusib: a pilot study. *Journal of Alzheimer's Disease,* 33, 205-215.

FUCHS, M., GENTLEMAN, E., SHAHID, S., HILL, R. G. & BRAUER, D. S. 2015. Therapeutic ion-releasing bioactive glass ionomer cements with improved mechanical strength and radiopacity. *Frontiers in Materials,* 2, 63.

GERSHON, S. & SOARES, J. C. 1997. Current therapeutic profile of lithium. *Archives of general psychiatry,* 54, 16-20.

GOLDBERG, M., KULKARNI, A. B., YOUNG, M. & BOSKEY, A. 2011. Dentin: Structure, Composition and Mineralization: The role of dentin ECM in dentin formation and mineralization. *Frontiers in bioscience (Elite edition),* 3, 711.

HAN, P., WU, C., CHANG, J. & XIAO, Y. 2012. The cementogenic differentiation of periodontal ligament cells via the activation of Wnt/β-catenin signalling pathway by Li+ ions released from bioactive scaffolds. *Biomaterials,* 33, 6370-6379.

ISHIMOTO, K., HAYANO, S., YANAGITA, T., KUROSAKA, H., KAWANABE, N., ITOH, S., ONO, M., KUBOKI, T., KAMIOKA, H. & YAMASHIRO, T. 2015. Topical application of lithium chloride on the pulp induces dentin regeneration. *PLoS One,* 10, e0121938.

KABACS, N., MEMON, A., OBINWA, T., STOCHL, J. & PEREZ, J. 2011. Lithium in drinking water and suicide rates across the East of England. *The British Journal of Psychiatry,* 198, 406-407.

KELLER, L., KUCHLER-BOPP, S., ACUNA MENDOZA, S., POLIARD, A. & LESOT, H. 2011. Tooth engineering: searching for dental mesenchymal cells sources. *Frontiers in physiology,* 2, 7.

KLEIN, P. S. & MELTON, D. A. 1996. A molecular mechanism for the effect of lithium on development. *Proceedings of the National Academy of Sciences,* 93, 8455-8459.

LIM, W. H., LIU, B., CHENG, D., HUNTER, D. J., ZHONG, Z., RAMOS, D. M., WILLIAMS, B. O., SHARPE, P. T., BARDET, C. & MAH, S. J. 2014. Wnt signaling regulates pulp volume and dentin thickness. *Journal of Bone and Mineral Research,* 29, 892-901.

MEIJER, L., FLAJOLET, M. & GREENGARD, P. 2004. Pharmacological inhibitors of glycogen synthase kinase 3. *Trends in pharmacological sciences,* 25, 471-480.

MIGUEZ-PACHECO, V., BÜTTNER, T., MACON, A., JONES, J., FEY, T., DE LIGNY, D., GREIL, P., CHEVALIER, J., MALCHERE, A. & BOCCACCINI, A. 2016. Development and characterization of lithium-releasing silicate bioactive glasses and their scaffolds for bone repair. *Journal of Non-Crystalline Solids,* 432, 65-72.

NEVES, V. & SHARPE, P. 2018. Regulation of reactionary dentine formation. *Journal of dental research,* 97, 416-422.

NEVES, V. C., BABB, R., CHANDRASEKARAN, D. & SHARPE, P. T. 2017. Promotion of natural tooth repair by small molecule GSK3 antagonists. Scientific reports, 7, 39654.

SEVERUS, W., KLEINDIENST, N., SEEMÜLLER, F., FRANGOU, S., MÖLLER, H. & GREIL, W. 2008. What is the optimal serum lithium level in the long-term treatment of bipolar disorder—a review? *Bipolar disorders,* 10, 231-237.

SHAN, T., ZHOU, C., YANG, R., YAN, F., ZHANG, P., FU, Y. & JIANG, H. 2015. Lithium chloride promotes the odontoblast differentiation of hair follicle neural crest cells by activating Wnt/β-catenin signaling. *Cell biology international,* 39, 35-43.

SMITH, D. C. 1998. Development of glass-ionomer cement systems. *Biomaterials,* 19, 467-478.

TOLOSA, E., LITVAN, I., HÖGLINGER, G. U., BURN, D., LEES, A., ANDRÉS, M. V., GÓMEZ-CARRILLO, B., LEÓN, T., DEL SER, T. & INVESTIGATORS, T. 2014. A phase 2 trial of the GSK-3 inhibitor tideglusib in progressive supranuclear palsy. *Movement Disorders,* 29, 470-478.

TYLKOWSKI, M., BRAUER, D. S. 2013. Mixed alkali effects in Bioglass 45S5. *Journal of Non-Crystalline Solids,* 376, 175-181

VISHWAKARMA, A., SHARPE, P., SHI, S. & RAMALINGAM, M. 2014. *Stem cell biology and tissue engineering in dental sciences,* Academic Press.

WASSON, E. A. & NICHOLSON, J. W. 1990. A study of the relationship between setting chemistry and properties of modified glass-poly (alkenoate) cements. *British Polymer Journal,* 23, 179-183.

WHYTE, J. L., SMITH, A. A. & HELMS, J. A. 2012. Wnt signaling and injury repair. *Cold Spring Harbor perspectives in biology,* 4, a008078.

WILSON, A. D. & KENT, B. 1971. The glass-ionomer cement, a new translucent dental filling material. *Journal of Applied Chemistry and Biotechnology,* 21, 313-313.

WILSON, A. D. & KENT, B. E. 1970. Dental silicate cements: IX. decomposition of the powder. *Journal of dental research,* 49, 7-13.

ZHANG, K., ALAOHALI, A., SAWANGBOON, N., SHARPE, P. T., BRAUER, D. S. & GENTLEMAN, E. 2019. A comparison of lithium-substituted phosphate and borate bioactive glasses for mineralised tissue repair. *Dental Materials,* 35, 919-927.

The invention claimed is:

1. A method of dentistry comprising administering a single dental filling material or precursor thereof to a subject in need thereof, wherein said dental filling material both stimulates dentine regeneration and provides a filling in the cavity at the same time, said dental filling material comprises lithium and said dental filling material is configured to release the lithium under physiological conditions, and wherein said method of dentistry comprises the treatment of a dental lesion, wherein the pulp is not exposed.

2. The method according to claim 1, wherein said method of dentistry comprises dentine repair.

3. The method according to claim 1, wherein said method of dentistry comprises the treatment of a dental lesion, wherein dentine is exposed but the pulp is not exposed.

4. The method according to claim 1, wherein the dental filling material or precursor thereof comprises a bioactive glass comprising lithium.

5. The method according to claim 4, wherein the bioactive glass comprises a source of lithium at a molar percentage of at least 1%.

6. The method according to claim 4, wherein the bioactive glass comprises $Li_2O$.

7. The method according to claim 4, wherein the bioactive glass comprises $Li_2O$ at a molar percentage of from 5 to 30%.

8. The method according to claim 1, wherein the dental filling material comprises a dental cement comprising lithium.

9. The method according to claim 8, wherein the dental cement is a glass ionomer cement comprising lithium.

10. The method according to claim 8, wherein the dental cement comprises a bioactive glass comprising lithium.

11. The method according to claim 10, wherein the bioactive glass is a bioactive glass comprising a source of lithium at a molar percentage of at least 1%.

12. The method according to claim 6, wherein the dental filling material or precursor thereof comprises the bioactive glass in an amount of at least 1 wt %.

13. The method of claim 4, wherein the dental filling material or precursor thereof comprises a glass component comprising the bioactive glass comprising lithium.

14. The method of claim 13, wherein the dental filling material or precursor thereof comprises the glass component in an amount of at least 10 wt %.

15. The method of claim 13, wherein the glass component comprises the bioactive glass in an amount of at least 1 wt %.

16. The method of claim 1, wherein a precursor of the dental filling material is administered.

17. The method according to claim 16, wherein the precursor is a dry precursor.

18. The method according to claim 16, wherein the precursor comprises a powder.

19. The method according to claim 16, wherein the precursor is provided in the form of a capsule, which capsule further comprises a liquid.

* * * * *